United States Patent
Anderson et al.

(10) Patent No.: US 10,449,362 B2
(45) Date of Patent: Oct. 22, 2019

(54) EXTRA-CARDIOVASCULAR CARDIAC PACING SYSTEM FOR DELIVERING COMPOSITE PACING PULSES

(71) Applicant: Medtronic, Inc., Minneapolis, MN (US)

(72) Inventors: David A. Anderson, Stanchfield, MN (US); Mark T. Marshall, Forest Lake, MN (US); Vladimir P. Nikolski, Blaine, MN (US); Robert T. Sawchuk, Roseville, MN (US); Amy E. Thompson-Nauman, Ham Lake, MN (US); John D. Wahlstrand, Shoreview, MN (US); Gregory A. Younker, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 389 days.

(21) Appl. No.: 15/368,197

(22) Filed: Dec. 2, 2016

(65) Prior Publication Data
US 2017/0157399 A1 Jun. 8, 2017

Related U.S. Application Data

(60) Provisional application No. 62/262,412, filed on Dec. 3, 2015.

(51) Int. Cl.
*A61N 1/00* (2006.01)
*A61N 1/362* (2006.01)
(Continued)

(52) U.S. Cl.
CPC ......... *A61N 1/3621* (2013.01); *A61N 1/3622* (2013.01); *A61N 1/36521* (2013.01);
(Continued)

(58) Field of Classification Search
CPC .. A61N 1/3621; A61N 1/3962; A61N 1/3752; A61N 1/36521; A61N 1/3622; A61N 1/371
See application file for complete search history.

(56) References Cited

U.S. PATENT DOCUMENTS

| | | |
|---|---|---|
| 5,184,616 A | 2/1993 | Weiss |
| 5,215,083 A | 6/1993 | Drane et al. |

(Continued)

FOREIGN PATENT DOCUMENTS

WO 2009006321 A2 1/2009

OTHER PUBLICATIONS (PCT/US2016/064762) PCT Notification of Transmittal of the International Search Report and the Written Opinion of the International Searching Authority, dated Mar. 30, 2017, 11 pages.
(Continued)

*Primary Examiner* — Mallika D Fairchild

(57) ABSTRACT

An implantable medical device is configured to control a therapy module to couple a capacitor array comprising a plurality of capacitors to a plurality of extra-cardiovascular electrodes and control the therapy module to deliver a composite pacing pulse to a patient's heart via the plurality of extra-cardiovascular electrodes by sequentially discharging at least a portion of the plurality capacitors to produce a series of at least two individual pulses that define the composite pacing pulse.

32 Claims, 16 Drawing Sheets

(51) Int. Cl.
*A61N 1/365* (2006.01)
*A61N 1/37* (2006.01)
*A61N 1/375* (2006.01)
*A61N 1/39* (2006.01)

(52) U.S. Cl.
CPC ........... *A61N 1/371* (2013.01); *A61N 1/3752* (2013.01); *A61N 1/3962* (2013.01)

(56) References Cited

U.S. PATENT DOCUMENTS

| | | | |
|---|---|---|---|
| 5,824,018 | A | 10/1998 | Dreher et al. |
| 6,778,860 | B2 | 8/2004 | Ostroff et al. |
| 6,856,835 | B2 | 2/2005 | Bardy et al. |
| 6,865,417 | B2 | 3/2005 | Rissman et al. |
| 6,952,608 | B2 | 10/2005 | Ostroff |
| 6,952,610 | B2 | 10/2005 | Ostroff et al. |
| 6,954,670 | B2 | 10/2005 | Ostroff |
| 7,092,754 | B2 | 8/2006 | Bardy et al. |
| 7,146,212 | B2 | 12/2006 | Bardy et al. |
| 7,184,833 | B2 | 2/2007 | Ganion et al. |
| 7,389,139 | B2 | 6/2008 | Ostroff |
| 7,392,081 | B2 | 6/2008 | Wagner et al. |
| 7,471,983 | B2 | 12/2008 | Voegele et al. |
| 7,502,645 | B2 | 3/2009 | Ostroff et al. |
| 7,522,957 | B2 | 4/2009 | Ostroff |
| 7,751,885 | B2 | 7/2010 | Bardy et al. |
| 7,761,150 | B2 | 7/2010 | Ghanem et al. |
| 8,036,742 | B2 | 10/2011 | Sullivan et al. |
| 8,155,740 | B2 | 4/2012 | Wanasek |
| 8,195,291 | B2 | 6/2012 | Norton et al. |
| 8,359,094 | B2 | 1/2013 | Bonner et al. |
| 8,412,320 | B2 | 4/2013 | Ostroff et al. |
| 8,452,399 | B2 | 5/2013 | Wanasek |
| 8,758,365 | B2 | 6/2014 | Bonner et al. |
| 8,914,105 | B2 | 12/2014 | Wanasek |
| 2004/0215258 | A1 | 10/2004 | Lovett et al. |
| 2009/0210021 | A1 | 8/2009 | Ostroff |
| 2011/0319956 | A1* | 12/2011 | Zhu ................... A61N 1/056 607/25 |
| 2012/0191154 | A1 | 7/2012 | Ryu et al. |
| 2012/0197330 | A1 | 8/2012 | Crutchfield et al. |
| 2014/0088656 | A1* | 3/2014 | Cabelka ............. A61N 1/362 607/2 |
| 2015/0306375 | A1 | 10/2015 | Begon et al. |
| 2015/0306410 | A1 | 10/2015 | Marshall et al. |
| 2016/0158567 | A1 | 6/2016 | Marshall et al. |

OTHER PUBLICATIONS

Thompson-Nauman et al., "Extra-Cardiovascular Cardiac Pacing System", U.S. Appl. No. 14/957,651, filed Dec. 3, 2015, 65 pages.

* cited by examiner

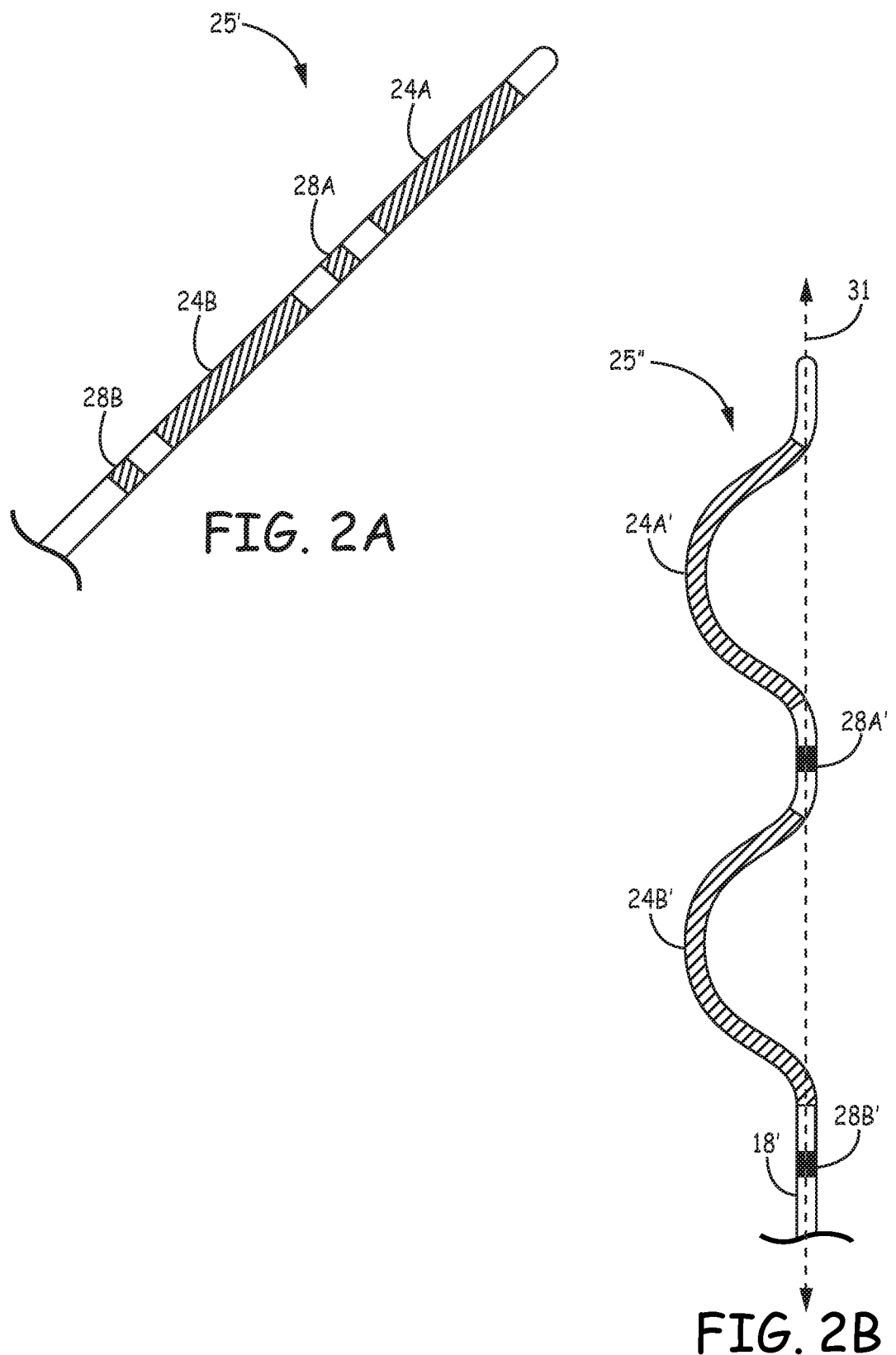

EXTRA-CARDIOVASCULAR CARDIAC PACING SYSTEM FOR DELIVERING COMPOSITE PACING PULSES

REFERENCE TO RELATED APPLICATION

This application claims the benefit of U.S. Provisional Application No. 62/262,412, filed provisionally on Dec. 3, 2015, the content of which is incorporated herein by reference in its entirety.

TECHNICAL FIELD

The disclosure relates generally to implantable medical devices and, in particular, to a system, device and method for delivering cardiac pacing pulses using extra-cardiovascular electrodes.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to position electrodes or other sensors at desired locations for delivery of electrical stimulation or sensing of physiological conditions. For example, electrodes or sensors may be carried along a distal portion of a lead that is extended subcutaneously, transvenously, or submuscularly. A proximal portion of the lead may be coupled to an implantable medical device housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to deliver electrical stimulation pulses to the heart to address abnormal cardiac rhythms.

IMDs capable of delivering electrical stimulation for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm. For example, a pacemaker or ICD may deliver low voltage pacing pulses to the heart upon detecting bradycardia or tachycardia using endocardial or epicardial electrodes. An ICD may deliver high voltage cardioversion or defibrillation shocks to the heart upon detecting fast ventricular tachycardia or fibrillation using electrodes carried by transvenous leads or non-transvenous leads. The type of therapy delivered and its effectiveness in restoring a normal rhythm depends at least in part on the type of electrodes used to deliver the electrical stimulation and their location relative to heart tissue.

SUMMARY

In general, the disclosure is directed to techniques for delivering extra-cardiovascular pacing pulses by an implantable medical device. A pacemaker or ICD operating according to the techniques disclosed herein delivers a series of fused low voltage electrical pulses using extra-cardiovascular electrodes to produce a composite cardiac pacing pulse defined by the fused low voltage pulses. A composite pacing pulse delivered using extra-cardiovascular electrodes may capture the heart when the cumulative pulse energy of the individual pulses exceeds a capture threshold of the heart, even when the individual pulse energies are less than the capture threshold.

In one example, the disclosure provides an implantable medical device comprising a pacing control module and a therapy module. The therapy module has a capacitor array comprising multiple capacitors and is configured to couple the capacitor array to extra-cardiovascular electrodes to deliver a composite pacing pulse to a patient's heart. The pacing control module is coupled to the therapy module and configured to control the therapy module to sequentially discharge at least a portion of the capacitors to produce a series of at least two individual pulses that define the composite pacing pulse.

In another example, the disclosure provides a method performed by an implantable medical device. The method includes controlling a therapy module to couple a capacitor array comprising multiple capacitors to extra-cardiovascular electrodes and controlling the therapy module by a pacing control module to deliver a composite pacing pulse to a patient's heart via the extra-cardiovascular electrodes by sequentially discharging at least a portion of the capacitors to produce a series of at least two individual pulses that define the composite pacing pulse.

In another example, the disclosure provides a non-transitory, computer-readable storage medium comprising a set of instructions which, when executed by a control module of an implantable medical device, cause the implantable medical device to control a therapy module to couple a capacitor array comprising multiple capacitors to extra-cardiovascular electrodes and control the therapy module to deliver a composite pacing pulse to a patient's heart via the extra-cardiovascular electrodes by sequentially discharging at least a portion of the capacitors to produce a series of at least two individual pulses that define the composite pacing pulse.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 2A is a conceptual diagram illustrating a distal portion of another example of the implantable electrical lead of FIG. 1A, having an alternative electrode arrangement.

FIG. 2B is a conceptual diagram illustrating a distal portion of another example of the extra-cardiovascular lead of FIG. 1A having an electrode arrangement similar to that of FIG. 2A but with a differently shaped lead body along a distal portion.

DETAILED DESCRIPTION

Figure 1A:
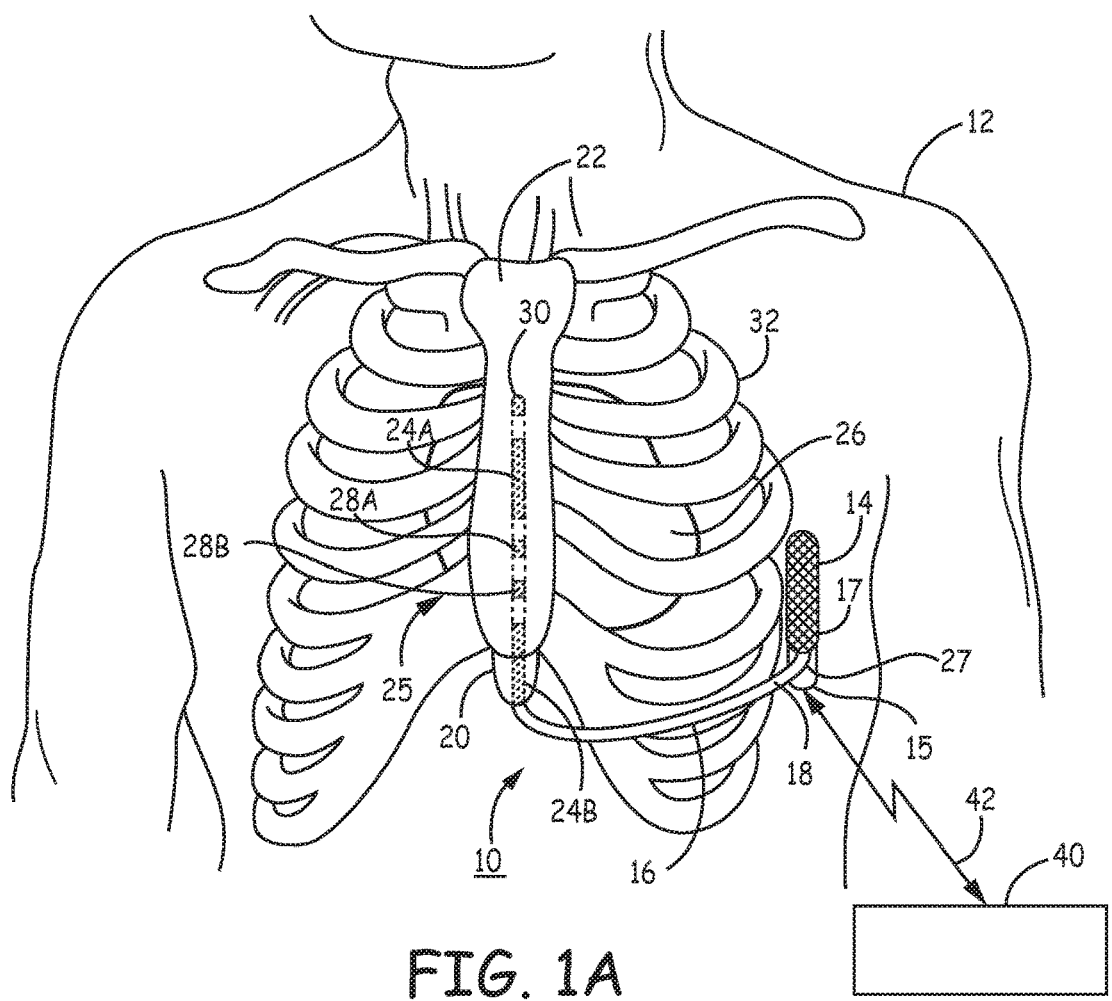
FIGS. 1A-1B are a conceptual diagrams of a patient implanted with an IMD system including a subcutaneously implanted IMD coupled to an extra-cardiovascular sensing, pacing and cardioversion/defibrillation lead for delivering extra-cardiovascular pacing pulses.

In general, this disclosure describes techniques for delivering low voltage pacing pulses using extra-cardiovascular electrodes that are not directly contacting cardiac tissue. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but not in intimate contact with myocardial tissue.

Pacing pulses delivered by endocardial or epicardial electrodes are generally not painful to a patient. Pacing pulses delivered by extra-cardiovascular electrodes may cause extra-cardiac capture of nerves and recruitment of skeletal muscle that may cause a noticeable sensation to the patient and, in some instances, pain or discomfort to the patient depending on the voltage amplitude of the pacing pulses. The pulse voltage amplitude required to capture the heart when pacing with extra-cardiovascular electrodes, such as subcutaneous or submuscular electrodes, may exceed an acceptable comfort level for the patient for a given pacing pulse width. A pacing pulse having a lower voltage amplitude when delivered by extra-cardiovascular electrodes may require a relatively long pulse width in order to deliver sufficient energy to capture the heart. The long pulse width may be beyond the capacity of a typical low voltage pacing capacitor due to the relatively fast decay rate of the pulse amplitude. Since a pacing pulse is delivered as the pacing capacitor is discharged across the pacing electrode vector, the pacing pulse amplitude may decay below an effective voltage amplitude before the required pacing pulse width expires resulting in a pacing pulse having insufficient energy to capture the heart.

As disclosed herein, an implantable, extra-cardiovascular medical device system is configured to deliver multiple individual electrical pulses in succession within a selected pacing pulse width to produce a composite, low voltage pacing pulse having an overall pulse width that is long enough to successfully pace the heart and a low enough pulse amplitude that, if perceptible by the patient, is acceptable. The composite pacing pulse may be delivered using extra-cardiovascular pacing electrodes that are not in direct contact with the myocardial tissue. The energy of each individual pulse is "fused" in time or cumulative in effect to produce a total pulse energy within the composite pulse width that is adequate to cause depolarization of myocardial tissue even when each individual pulse if delivered alone is inadequate to cause capture of the myocardial tissue.

The techniques disclosed herein may be implemented in any implantable pacemaker or ICD and particularly in a pacemaker or ICD coupled to extra-cardiovascular electrodes. The electrodes may be carried by a medical electrical lead extending from the pacemaker or ICD and/or carried by the housing of the pacemaker or ICD. The techniques disclosed herein are not necessarily limited to implantable systems and may be implemented in an external pacemaker or ICD using cutaneous surface electrodes or transcutaneous electrodes.

Figure 1B:
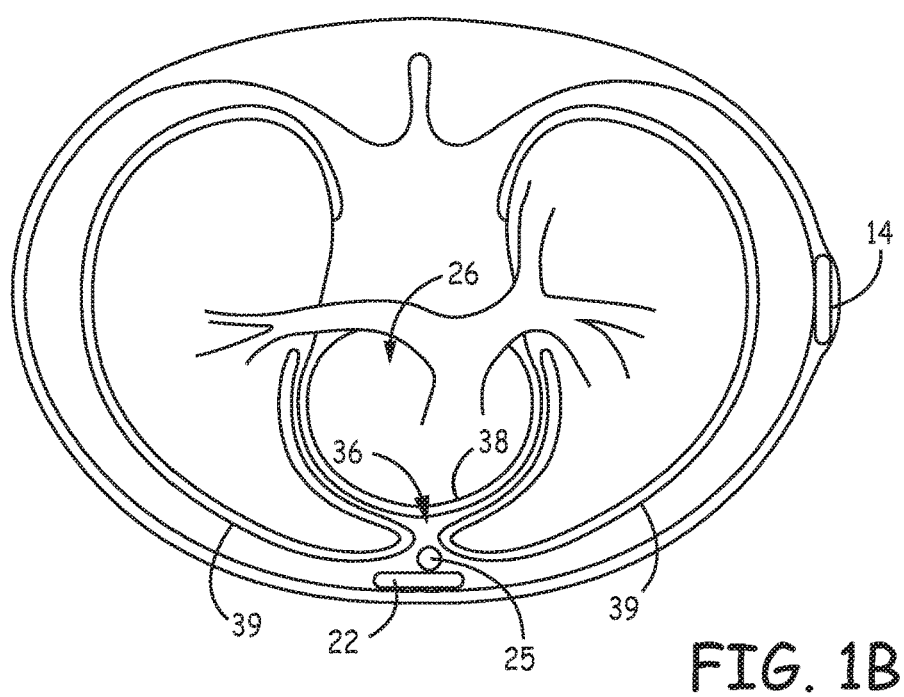

FIGS. 1A and 1B are conceptual diagrams of a patient 12 implanted with an extra-cardiovascular IMD system 10 that includes a subcutaneously implanted IMD 14 coupled to an extra-cardiovascular sensing, pacing and cardioversion/defibrillation (CV/DF) lead 16. FIG. 1A is a frontal view of patient 12 and FIG. 1B is a transverse view of patient 12. In the illustrative embodiment of FIGS. 1A and 1B, IMD 14 is an ICD configured for delivering high-voltage cardioversion/defibrillation (CV/DF) shocks in addition to the low-voltage, extra-cardiovascular pacing pulses delivered using the techniques disclosed herein.

IMD 14 includes a housing 15 and connector assembly 17 for receiving extra-cardiovascular lead 16. IMD 14 acquires cardiac electrical signals from heart 26 using electrodes carried by lead 16 and is configured to deliver cardiac pacing pulses to heart 26 using extra-cardiovascular electrodes carried by lead 16. As will be described herein, IMD 14 includes a pacing control module that controls an array of pacing capacitors to deliver composite pacing pulses each comprising a series of fused low-voltage pulses. The composite pacing pulse has a pulse amplitude that may be set to a comfortable level to the patient, e.g., less than 20 V, and a pulse width that is long enough to successfully capture and pace the heart using extra-cardiovascular electrodes.

The cardiac electrical signals received by IMD 14 are used for determining the patient's heart rhythm and providing appropriate pacing therapy as needed, such as bradycardia pacing, anti-tachycardia pacing (ATP), or pacing to treat asystole due to atrioventricular conduction block or following a cardioversion or defibrillation shock, for example. When IMD 14 is embodied as an ICD, it is configured to detect shockable rhythms, e.g., non-sinus, fast ventricular tachycardia and ventricular fibrillation, and deliver CV/DF shock therapy via defibrillation electrodes 24A and/or 24B carried by lead 16. In other examples, IMD 14 may be configured as a pacemaker for delivering low voltage pacing therapies without the capability of delivering high voltage CV/DF shock therapy. In that case, lead 16 may not include the defibrillation electrodes 24A and 24B.

Lead 16 includes a proximal end 27 that is connected to IMD 14 and a distal portion 25 that carries electrodes 24A, 24B, 28A, 28B and 30. All or a portion of housing 15 of IMD 14 may be formed of a conductive material, such as titanium or titanium alloy, and coupled to internal IMD circuitry to function as an electrode, sometimes referred to as a "CAN electrode."

Electrodes 24A and 24B are referred to as defibrillation electrodes because they may be used together or in combination with the conductive housing 15 of IMD 14 for delivering high voltage CV/DF shocks. Electrodes 24A and 24B may be elongated coil electrodes and generally have a relatively high surface area for delivering high voltage electrical stimulation pulses compared to low voltage pacing and sensing electrodes 28A, 28B and 30. However, electrodes 24A and 24B may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24A and 24B to use in only high voltage CV/DF therapy applications. As described herein, electrodes 24A and/or 24B may be used in a pacing electrode vector for delivering composite extra-cardiovascular pacing pulses.

In some cases, defibrillation electrodes 24A and 24B may together form a defibrillation electrode in that they are configured to be activated concurrently. Alternatively, defibrillation electrodes 24A and 24B may form separate defibrillation electrodes in which case each of the electrodes 24A and 24B may be activated independently. In some instances, defibrillation electrodes 24A and 24B are coupled to electrically isolated conductors, and IMD 14 may include switching mechanisms to allow electrodes 24A and 24B to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive). In other examples, lead 16 may include a single defibrillation electrode rather than two defibrillation electrodes as shown.

Electrodes 28A, 28B and 30 are relatively smaller surface area electrodes for delivering low voltage pacing pulses and for sensing cardiac electrical signals. Electrodes 28A, 28B and 30 are referred to as pace/sense electrodes because they are generally configured for use in low voltage applications, e.g., used as either a cathode or anode for delivery of pacing pulses and/or sensing of cardiac electrical signals. In some instances, electrodes 28A, 28B, and 30 may provide only pacing functionality, only sensing functionality or both.

In the example illustrated in FIGS. 1A and 1B, electrodes 28A and 28B are located between defibrillation electrodes 24A and 24B and electrode 30 is located distal to defibrillation electrode 24A. Electrodes 28A and 28B are illustrated as ring electrodes, and electrode 30 is illustrated as a hemispherical tip electrode in the example of FIG. 1A. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along lead body 18. Further, electrodes 28A, 28B, and 30 may be of similar type, shape, size and material or may differ from each other.

An ECG signal may be acquired using a sensing vector including any combination of electrodes 28A, 28B, 30 and housing 15. In some examples, a sensing vector may even include defibrillation electrodes 24A and/or 24B. IMD 14 may include more than one sensing channel such that sensing electrode vectors may be selected two at a time by IMD 14 for monitoring for a shockable rhythm or determining a need for cardiac pacing.

Pacing pulses may be delivered using any combination of electrodes 24A, 24B, 28A, 28B, 30 and housing 15. The pacing electrode vector selected for delivering pacing pulses may be selected based on pacing electrode vector impedance measurements and capture threshold testing. For example, a pacing vector may be selected from among electrodes 24A, 24B, 28A, 28B, 30 and housing 15 that has the lowest impedance and/or the lowest composite pacing pulse width that captures the heart for a programmed pacing pulse voltage amplitude. The pacing pulse voltage amplitude may be programmed to be below a threshold for pain and discomfort, which may be based on individual patient testing and/or clinical data. In some examples, a pacing electrode vector is selected between one of pace/sense electrodes 28A, 28B or 30 and one of the defibrillation electrodes 24A or 24B. In other examples, a pacing electrode vector is selected between two of the pace/sense electrodes 28A, 28B and/or 30. Selection of a pacing electrode vector between two electrodes carried by the distal portion 25 of lead 16 may reduce skeletal muscle recruitment when extra-cardiovascular pacing pulses are delivered compared to a pacing vector that includes IMD housing 15.

In some instances, electrodes 24A, 24B, 28A, 28B, and/or 30 of lead 16 may be shaped, oriented, designed or otherwise configured to reduce extra-cardiac stimulation. For example, electrodes 24A, 24B and/or electrodes 28A, 28B, and/or 30 of lead 16 may be shaped, oriented, designed, partially insulated or otherwise configured to focus, direct or point electrodes 24A, 24B and/or electrodes 28A, 28B, and/or 30 toward heart 26. In this manner, electrical stimulation pulses delivered via lead 16 are directed toward heart 26 and not outward toward skeletal muscle. For example, electrodes 24A, 24B and/or electrodes 28A, 28B, and/or 30 of lead 16 may be partially coated or masked with a polymer (e.g., polyurethane) or another coating material (e.g., tantalum pentoxide) on one side or in different regions so as to direct the electrical energy toward heart 26 and not outward toward skeletal muscle. In the case of a ring electrode, for example, the ring electrode may be partially coated with the polymer or other material to form a half-ring electrode, quarter-ring electrode, or other partial-ring electrode. When IMD 14 delivers pacing pulses via electrodes 24A, 24B, 28A, 28B, and/or 30, recruitment of surrounding skeletal muscle by the pacing pulses, which can cause discomfort to the patient, may be reduced by shaping, orienting, or partially insulating electrodes to focus or direct electrical energy toward heart 26.

In various examples, electrodes 24A, 24B, 28A, 28B and 30 may be carried along lead 16 at other locations than those shown and in different arrangements relative to each other but are generally positioned to acquire cardiac electrical signals having acceptable cardiac signal strength for sensing cardiac events, such as R-wave signals that occur upon depolarization of the ventricles, and for delivering low-voltage pacing pulses for successfully capturing the patient's heart 26. While three pace/sense electrodes 28A, 28B and 30 are shown along lead 16, lead 16 may carry more or fewer pace/sense electrodes in other examples. Other arrangements of defibrillation and pace/sense electrodes carried by an extra-cardiovascular lead that may be used for delivering composite pacing pulses as described herein are generally disclosed in pending U.S. Pat. Publication No. 2015/0306375 (Marshall, et al.) and U.S. Pat. Publication No. 2015/0306410 (Marshall, et al.), both of which are incorporated herein by reference in their entirety. In still other examples, lead 16 may carry a single pace/sense electrode to serve as a pacing cathode (or anode) electrode with housing 15 or a defibrillation electrode, e.g., defibrillation electrode 24A or 24B, serving as a return anode (or cathode) electrode.

In other examples, dedicated pacing electrodes and separate, dedicated sensing electrodes may be carried by lead 16 or another lead coupled to IMD 14. It is understood that one or more leads may be coupled to IMD 14 for connecting at least one defibrillation electrode and at least one pacing and sensing electrode to IMD 14 for monitoring cardiac electrical signals, delivering pacing pulses and delivering CV/DF shock therapy when IMD 14 is configured as an ICD. Pacing therapies that may be delivered by IMD 14 using any of electrodes 24A, 24B, 28A, 28B, 30 and housing 15 may include, but are not limited to, bradycardia pacing, ATP, post-shock pacing for treating bradycardia or asystole after a CV/DF shock, pacing during asystole due to atrioventricular conduction block. Additionally or alternatively, composite pulses delivered according to the techniques disclosed herein using any of electrodes 24A, 24B, 28A, 28B, 30 and/or housing 15 may be entrainment pulses delivered prior to a T-shock for inducing a tachyarrhythmia or pulses included in a high frequency burst of pulses (e.g., at 50 Hz) for inducing tachyarrhythmia, e.g., for the purposes of testing anti-tachyarrhythmia therapies in a clinical setting. The methods disclosed herein for delivering composite pacing pulses may be used in conjunction with the tachyarrhythmia induction methods generally disclosed in U.S. Patent Application No. 62/262,500 and corresponding U.S. Pat. No. 10,046,168, both incorporated herein by reference in their entirety.

FIG. 1B is a transverse view of patient 12 showing the distal portion 25 of lead 16 extending substernally, e.g., at least partially in or adjacent to the anterior mediastinum 36. Lead 16 is illustrated in FIGS. 1A and 1B as being implanted at least partially in a substernal location, e.g., between the heart and ribcage 32 or sternum 22. In one such configuration, the proximal portion of lead 16 extends subcutaneously from IMD 14 (which is implanted near a midaxillary line on the left side of patient 12) toward sternum 22. At a location near xiphoid process 20, lead 16 bends or turns superiorly and distal portion 25 of lead 16, which carries electrodes 24A, 24B, 28A, 28B and 30, extends substernally, under or below the sternum 22 in the anterior mediastinum 36.

Anterior mediastinum 36 is bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion of lead 16 extends along the posterior side of sternum 22 substantially within the loose connective tissue and/or substernal musculature of anterior mediastinum 36. Lead 16 may be at least partially implanted in other extra-cardiovascular, intrathoracic locations, e.g., along ribcage 32 or along or adjacent to the perimeter of the pericardium or within the pleural cavity.

IMD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which IMD 14 is implanted pectorally, lead 16 may follow a different path, e.g., across the upper chest area and inferior along sternum 22. When the IMD 14 is implanted in the pectoral region, the system 10 may include a second lead that extends along the left side of the patient and includes a defibrillation electrode and/or one or more pacing electrodes positioned along the left side of the patient to function as an anode or cathode of a therapy delivery vector including another electrode located anteriorly for delivering electrical stimulation to heart 26 positioned there between.

Figure 1C:
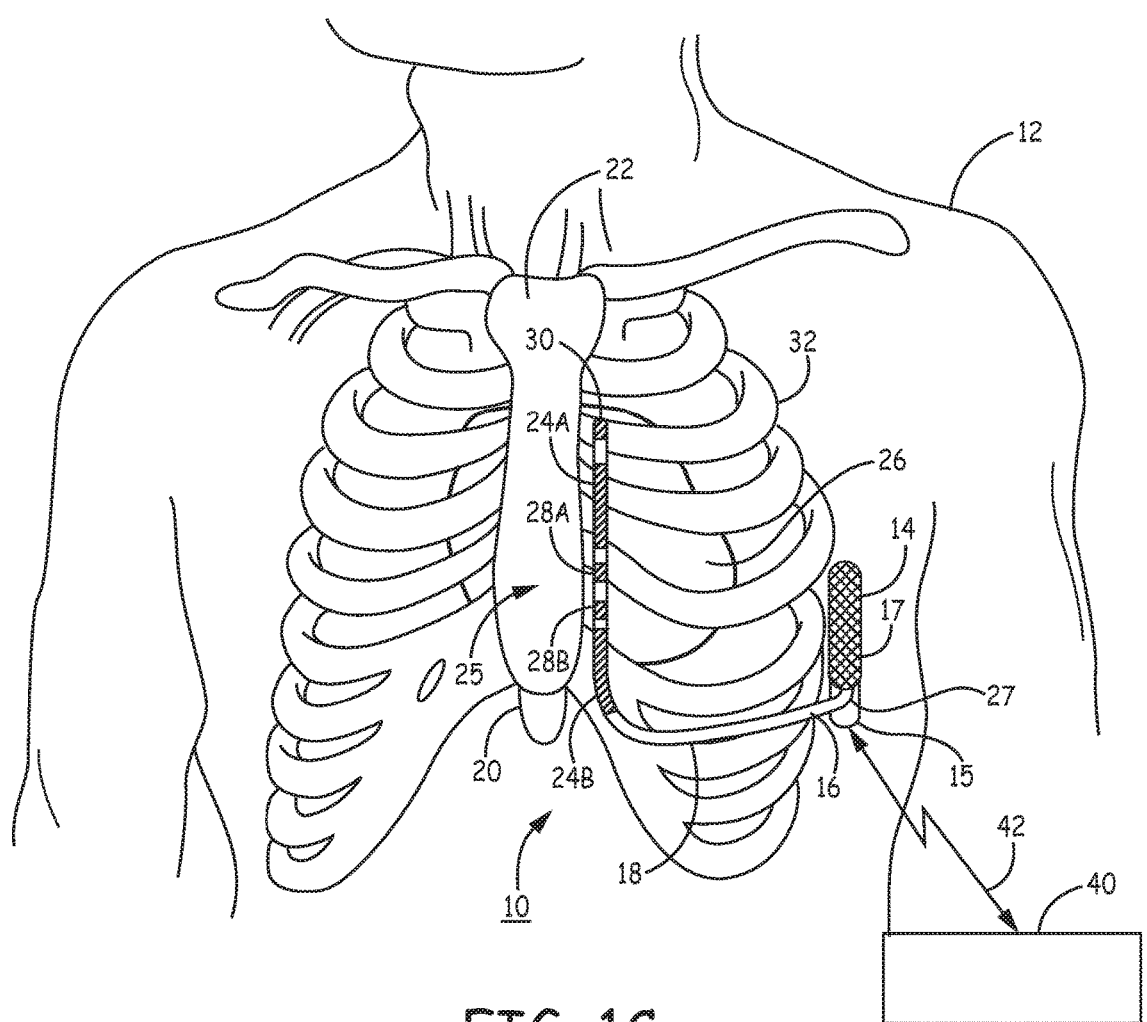
FIG. 1C is a schematic diagram of an alternative implant location of the extra-cardiovascular sensing, pacing and cardioversion/defibrillation lead of the IMD system of FIG. 1A.

FIG. 1C is a schematic diagram of an alternative implant location of lead 16. In other examples, the distal portion of lead 16 may be implanted at other extra-cardiovascular locations than the substernal location shown in FIG. 1A. For instance, as shown in FIG. 1C, lead 16 may be implanted subcutaneously or submuscularly, between the skin and the ribcage 32 or between the skin and sternum 22. Lead 16 may extend subcutaneously from IMD 14 toward xiphoid process 20 as shown in FIG. 1A, but instead of extending substernally, along the posterior side of sternum 22, lead 16 may bend or turn at a location near xiphoid process 20 and extend subcutaneously or submuscularly superior, over sternum 22 and/or ribcage 32. The distal portion 25 of lead 16 may be parallel to sternum 22 or laterally offset from sternum 22, to the left or the right. In other examples, the distal portion 25 of lead 16 may be angled laterally away from sternum 22, either to the left or the right, such that the distal portion 25 extends non-parallel to sternum 22.

In another example, IMD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of IMD 14 laterally and posterially to the patient's back to a location opposite heart 26 such that the heart 26 is generally disposed between the IMD 14 and electrodes 24A, 24B, 28A, 28B and 30. The techniques disclosed herein for generating low voltage pacing pulses for pacing the heart using extra-cardiovascular electrodes are not limited to a particular subcutaneous, submuscular, supra-sternal, substernal or intra- or extra-thoracic location of the extra-cardiovascular electrodes.

Referring again to FIG. 1A, lead 16 includes an elongated lead body 18 that carries the electrodes 24A, 24B, 28A, 28B and 30 and insulates elongated electrical conductors (not illustrated) that extend from a respective electrode 24A, 24B, 28A, 28B and 30 through the lead body 18 to a proximal connector (not shown) that is coupled to connector assembly 17 of IMD 14 at lead proximal end 27. Lead body 18 may be formed from a non-conductive material, such as silicone, polyurethane, fluoropolymers, or mixtures thereof or other appropriate materials, and is shaped to form one or more lumens within which the one or more conductors extend. The conductors are electrically coupled to IMD circuitry, such as a therapy delivery module and/or a sensing module, via connections in IMD connector assembly 17 that includes a connector bore for receiving the proximal connector of lead 16 and associated electrical feedthroughs crossing IMD housing 15. The electrical conductors transmit electrical stimulation therapy from a therapy delivery module within IMD 14 to one or more of electrodes 24A, 24B, 28A, 28B and/or 30 and transmit cardiac electrical signals from one or more of electrodes 24A, 24B, 28A, 28B and/or 30 to the sensing module within IMD 14.

Housing 15 forms a hermetic seal that protects internal electronic components of IMD 14. As indicated above, housing 15 may function as a "CAN electrode" since the conductive housing or a portion thereof may be electrically coupled to internal circuitry to be used as an indifferent or ground electrode during ECG sensing or during therapy delivery. As will be described in further detail herein, housing 15 may enclose one or more processors, memory devices, transmitters, receivers, sensors, sensing circuitry, therapy circuitry and other appropriate components.

The example system 10 of FIG. 1A is illustrative in nature and should not be considered limiting of the techniques described in this disclosure. The techniques disclosed herein may be implemented in numerous ICD or pacemakers and electrode configurations that include extra-cardiovascular electrodes for delivering cardiac pacing pulses. The IMD system 10 is referred to as an extra-cardiovascular IMD system because lead 16 is a non-transvenous lead, positioned outside the blood vessels, heart 26 and pericardium 38. The techniques disclosed herein may also be employed by a leadless device implanted substernally, intra-thoracically or extra-thoracically and having electrodes carried by the housing, and/or in some cases by a conductor extending from the housing. Another example of an IMD in which the presently disclosed techniques may be implemented is generally disclosed in U.S. Pat. No. 8,758,365 (Bonner, et al.), incorporated herein by reference in its entirety.

An external device 40 is shown in telemetric communication with IMD 14 by a communication link 42. External device 40 may include a processor, display, user interface, telemetry unit and other components for communicating with IMD 14 for transmitting and receiving data via communication link 42. Communication link 42 may be established between IMD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from IMD 14 and to program operating parameters and algorithms in IMD 14 for controlling IMD functions. External device 40 may be used to program cardiac rhythm detection parameters and therapy control parameters used by IMD 14. Data stored or acquired by IMD 14, including physiological signals or associated data derived therefrom, results of device diagnostics, and histories of detected rhythm episodes and delivered therapies, may be retrieved from IMD 14 by external device 40 following an interrogation command. External device 40 may alternatively be embodied as a home monitor or hand held device.

FIG. 2A is a conceptual diagram illustrating a distal portion 25' of another example of implantable electrical lead 16 having an alternative electrode arrangement. In this example, distal portion 25' includes two pace/sense electrodes 28A and 28B and two defibrillation electrodes 24A and 24B and respective conductors to provide the electrical stimulation and sensing functionality as described above in conjunction with FIG. 1A. In this example, however, electrode 28B is proximal to proximal defibrillation electrode 24B, and electrode 28A is distal to proximal defibrillation electrode 24B such that pace/sense electrodes 28A and 28B are separated by defibrillation electrode 24B. In a further example, in addition to electrodes 28A and 28B, lead 16 may include a third pace/sense electrode located distal to defibrillation electrode 24A. IMD 14 may deliver cardiac pacing pulses and/or sense electrical signals using any electrode vector that includes defibrillation electrodes 24A and/or 24B (individually or collectively), and/or electrodes 28A and/or 28B, and/or the housing 15 of IMD 14.

The spacing and location of pace/sense electrodes 28A and 28B may be selected to provide pacing vectors that enable efficient pacing of heart 26. The lengths and spacing of electrodes 24A, 24B, 28A and 28B may correspond to any of the examples provided in the above-incorporated references. For example, the distal portion 25' of lead 16 from the distal end to the proximal side of the most proximal electrode (e.g., electrode 28B in the example of FIG. 2A) may be less than or equal to 15 cm and may be less than or equal to 13 cm and or even less than or equal to 10 cm. It is contemplated that one or more pace/sense electrodes may be distal to distal defibrillation electrode 24A, one or more pace/sense electrodes may be between defibrillation electrodes 24A and 24B, and/or one or more pace/sense electrodes may be proximal to proximal defibrillation electrode 24B. Having multiple electrodes at different locations along lead body 18 enables selection from among a variety of inter-electrode spacings, which allows a pacing electrode pair (or combination) to be selected having an inter-electrode spacing that results in the greatest pacing efficiency.

FIG. 2B is a conceptual diagram illustrating a distal portion 25" of another example of extra-cardiovascular lead 16 having an electrode arrangement similar to that of FIG. 2A but with a non-linear or curving distal portion 25" of lead body 18'. Lead body 18' may be pre-formed to have a normally curving, bending, serpentine, undulating, or zig-zagging shape along distal portion 25". In this example, defibrillation electrodes 24A' and 24B' are carried along pre-formed curving portions of the lead body 18'. Pace/sense electrode 28A' is carried in between defibrillation electrodes 24A' and 24B'. Pace/sense electrode 28B' is carried proximal to the proximal defibrillation electrode 24B'.

In one example, lead body 18' may be formed having a curving distal portion 25" that includes two "C" shaped curves, which together may resemble the Greek letter epsilon, "ε." Defibrillation electrodes 24A' and 24B' are each carried by the two respective C-shaped portions of the lead body distal portion 25" and extend or curve in the same direction. In the example shown, pace/sense electrode 28A' is proximal to the C-shaped portion carrying electrode 24A', and pace/sense electrode 28B' is proximal to the C-shaped portion carrying electrode 24B'. Pace/sense electrodes 24A' and 24B' are approximately aligned with a central axis 31 of the straight, proximal portion of lead body 18' such that mid-points of defibrillation electrodes 24A' and 24B' are laterally offset from electrodes 28A' and 28B'. Defibrillation electrodes 24A' and 24B' are located along respective C-shaped portions of the lead body distal portion 25" that extend laterally in the same direction away from central axis 31 and electrodes 28A' and 28B'. Other examples of extra-cardiovascular leads including one or more defibrillation electrodes and one or more pacing and sensing electrodes carried by a curving, serpentine, undulating or zig-zagging distal portion of the lead body that may be implemented with the pacing techniques described herein are generally disclosed in pending U.S. Pat. Publication No. 2016/0158567 (Marshall, et al.), incorporated herein by reference in its entirety.

Figure 3:
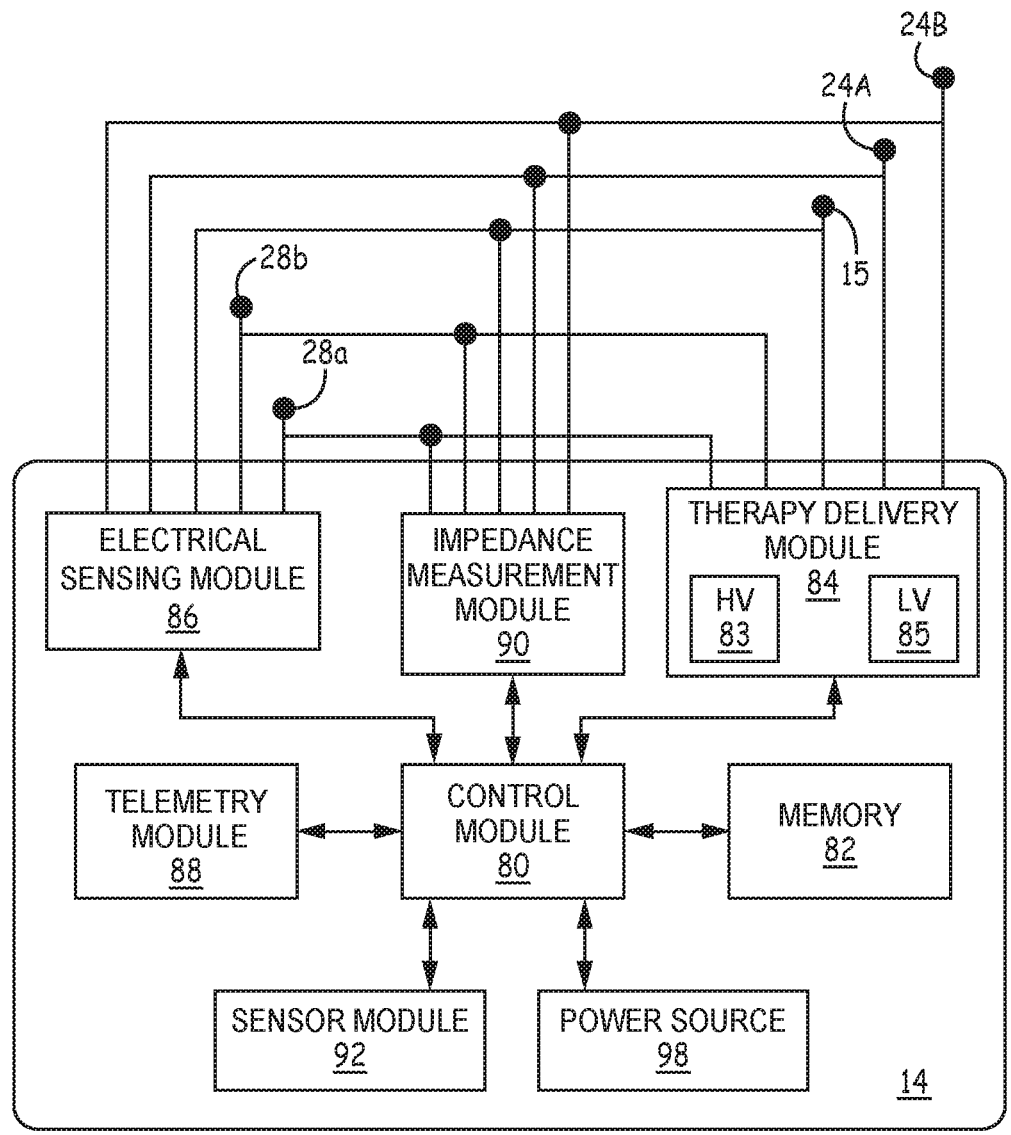
FIG. 3 is a schematic diagram of the IMD of FIG. 1A according to one example.

FIG. 3 is a schematic diagram of IMD 14 according to one example. The electronic circuitry enclosed within housing 15 (shown schematically as a can electrode in FIG. 5) includes software, firmware and hardware that cooperatively monitor one or more ECG signals, determine when a pacing therapy is necessary, and deliver prescribed pacing therapies as needed. When IMD 14 is configured as an ICD as illustrated herein, the software, firmware and hardware is also configured to determine when a CV/DF shock or cardiac pacing is necessary, and deliver prescribed CV/DF shock therapies or pacing therapies. IMD 14 may be coupled to a lead, such as lead 16 shown in any of the examples of FIGS. 1A, 1B, 1C, 2A and 2B, carrying extra-cardiovascular electrodes 24A, 24B, 28A, and 28B and in some examples electrode 30 (not shown in FIG. 3), for delivering pacing therapies, CV/DF shock therapies and sensing cardiac electrical signals.

IMD 14 includes a control module 80, memory 82, therapy delivery module 84, electrical sensing module 86, telemetry module 88, and may include an impedance measurement module 90 and an optional sensor module 92. A power source 98 provides power to the circuitry of IMD 14, including each of the modules 80, 82, 84, 86, 88, 90 and 92 as needed. Power source 98 may include one or more energy storage devices, such as one or more rechargeable or non-rechargeable batteries. Power source 98 is coupled to low voltage (LV) and high voltage (HV) charging circuits included in therapy delivery module 84 for charging LV and HV capacitors, respectively, included in therapy delivery module 84 for generating therapeutic electrical stimulation pulses.

The functional blocks shown in FIG. 3 represent functionality included in IMD 14 and may include any discrete and/or integrated electronic circuit components that implement analog and/or digital circuits capable of producing the functions attributed to IMD 14 herein. As used herein, the term "module" refers to an ASIC, an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the IMD. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, pacing therapy control operations performed by control module 80 may be implemented in a processor executing instructions stored in memory 82. IMD 14 may include more or fewer modules than shown in FIG. 3. For example impedance measuring module 90 and sensor module 92 may be optional and excluded in some instances. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other IMD modules to perform various functions attributed to IMD 14 or those IMD modules. The non-transitory computer readable media storing the instructions may include any of the media listed above.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 are electrically coupled to electrodes 24A, 24B, 28A, 28B carried by lead 16 and the housing 15, which may function as a common or ground electrode.

Electrical sensing module 86 is selectively coupled to electrodes 28A and 28B and housing 15 in order to monitor electrical activity of the patient's heart. Electrical sensing module 86 may additionally be selectively coupled to electrodes 24A and 24B. Sensing module 86 is enabled to selectively monitor one or more sensing vectors selected from the available electrodes 24A, 24B, 28A and 28B and housing 15. For example, sensing module 86 may include switching circuitry for selecting which of electrodes 24A, 24B, 28A and 28B and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing vectors selected from electrodes 24A, 24B, 28A and 28B and housing 15. Each sensing channel may be configured to amplify, filter and rectify the cardiac electrical signal received from selected electrodes coupled to the respective sensing channel to improve the signal quality for sensing cardiac events, e.g., R-waves and P-waves.

For example, each sensing channel in sensing module 86 may include an input or pre-filter and amplifier for receiving a cardiac electrical signal from a respective sensing vector, an analog-to-digital converter, a post-amplifier and filter, a rectifier to produce a digitized, rectified and amplified cardiac electrical signal that is passed to a cardiac event detector included in sensing module 86 and/or to control module 80. The cardiac event detector may include a sense amplifier, comparator or other circuitry for comparing the rectified cardiac electrical signal to a cardiac event sensing threshold, such as an R-wave sensing threshold, which may be an auto-adjusting threshold. Sensing module 84 may produce a sensed cardiac event signal in response to a sensing threshold crossing. Cardiac event sensing thresholds used by each sensing channel may be automatically adjusted according to sensing control parameters, which may be stored in memory 82.

Sensed event signals produced by electrical sensing module 86 may be used by control module 80 for detecting a shockable rhythm and/or for detecting a need for pacing. For example, control module 80 may respond to sensed event signals by setting pacing escape intervals for controlling the timing of pacing pulses delivered by therapy delivery module 84. In addition to the sensed cardiac event signals, electrical sensing module 86 may output a digitized ECG signal for use by control module 80 in detecting/confirming tachycardia, e.g., via a morphology or wavelet analysis.

Therapy delivery module 84 includes an LV therapy module 85 for delivering low voltage pacing pulses using an extra-cardiovascular pacing electrode vector selected from electrodes 24A, 24B, 28A and 28B and housing 15. The LV therapy module 85 includes an array of capacitors that are selectably controlled by control module 80 to provide a single composite pacing pulse comprising a series of two or more fused pulses delivered individually by sequentially discharging capacitors of the capacitor array within a composite pacing pulse width. Multiple capacitors may be selected one at a time in sequence to deliver the individual pulses included within a composite pacing pulse. In other instances, multiple capacitors may be selected two at a time to deliver each individual pulse of the composite pacing pulse. In various examples, two or more combinations of one or more capacitors are selected in timed sequence to deliver two or more sequentially fused pulses which collectively define the composite pacing pulse. As used herein, the term "fused pulses" refers to electrical pulses that are delivered sequentially within a composite pacing pulse width to produce a cumulative pulse energy sufficient to cause a pacing-evoked myocardial depolarization to capture the heart. The pulse energy of each individual one of the fused pulses may be insufficient to capture the heart, but the cumulative energy of the fused pulses delivered within the time envelope of the composite pacing pulse width is sufficient to cause a single evoked response of the myocardium.

LV capacitors included in the LV therapy module 85 are charged to a voltage according to a programmed pacing pulse amplitude by a LV charging circuit, which may include a state machine for charging the LV capacitors to a multiple of a battery charge included in power source 98, for example four times the battery charge. At an appropriate time, the LV therapy module 85 couples individual capacitors (or combinations of individual capacitors) of the capacitor array to a pacing electrode vector in timed sequence. The capacitor combinations are sequentially discharged to deliver a composite pacing pulse defined by the sequentially delivered individual pulses. The individually delivered pulses are fused in time such that the individual pulse energy is cumulative in producing a total pulse energy that is greater than the pacing capture threshold of the patient's heart, even though each individual pulse may have a pulse energy that is less than the pacing capture threshold. In some examples, the leading edge of an individual pulse delivered by one capacitor (or one combination of capacitors) occurs at (e.g., within inherent electrical circuitry timing limitations) or before the immediately preceding individual pulse reaches its terminating edge. In some cases, the individual pulses may be separated by a non-zero time gap within the composite pacing pulse width, however the cumulative electrical energy of the individual pulses within the composite pulse width is sufficient to capture the myocardium.

As described below, LV therapy module 85 may be configured to sample the composite pacing pulse amplitude in real time over the composite pacing pulse width. The next capacitor (or combination of capacitors) in the capacitor sequence may be coupled to the pacing electrode vector when the pulse amplitude of an individual pulse reaches a threshold amplitude. In this way, the composite pacing pulse amplitude is not allowed to fall below a predetermined minimum amplitude for the entirety of the composite pacing pulse width.

Impedance measurement module 90 may be electrically coupled to the available electrodes 24A, 24B, 28A and 28B and housing 15 for performing impedance measurements of one or more candidate pacing electrode vectors. Control module 80 may control impedance measurement module 90 to perform impedance measurements for use in selecting the pacing electrode vector. For example, control module 80 may pass a signal to impedance measurement module 90 to initiate an impedance measurement for a pacing electrode vector. Impedance measurement module 90 is configured to apply a drive or excitation current across a pacing electrode vector and determine the resulting voltage. The voltage signal may be used directly as the impedance measurement or impedance may be determined from the applied current and the measured voltage. The impedance measurement may be passed to control module 80 for use in selecting a pacing electrode vector for therapy delivery.

As described below, an impedance measurement may be used by control module 80 for selecting the number of individual pulses and/or the series of capacitors that will be discharged to produce the composite pacing pulse. The impedance of the selected pacing vector and the capacitance of a given capacitor or capacitor combination in the capacitor array will determine the decay rate of an individual pulse. If the impedance is relatively low, the individual pulse has a relatively fast decay rate. A fast decay of an individual pulse requires the next pulse in a series of fused pulses to occur early, before the first pulse decays below a minimum amplitude for a time period that would lead to loss of capture. The next capacitor (or capacitor combination) in the series may be required to begin discharging relatively earlier if the impedance is low and the decay rate is fast compared to when the impedance is high and the pacing pulse decay rate is relatively slower. The individual pulse width, therefore, may be longer when the impedance is relatively high, and the individual pulse width may be relatively shorter when the impedance is relatively low.

To achieve a desired overall pulse width and sustain the composite pulse amplitude above a minimum amplitude for all or a vast majority of the composite pulse width, the individual pulse width may be relatively short, and the pulse number may be increased when pacing vector impedance is low. Fewer relatively longer individual pulses may be delivered when the pacing vector impedance is relatively higher. The individual pulse width may be decreased and the individual pulse number may be increased in order to achieve a desired composite pulse width with a pulse amplitude that remains above a minimum amplitude threshold for each individual pulse width. The time interval from one leading edge to the next leading edge of the individual pulses and the total number of pulses will determine the overall composite pacing pulse width.

If the impedance is low, the decay time of the pulse may be lengthened by using a higher capacitance for delivering each individual pulse. The individual pulse width and pulse number may be kept the same, but the decay time is adjusted by selecting a capacitor or combination of capacitors having a higher capacitance value when pacing vector impedance is low. Accordingly, impedance measurements from impedance measurement module 90 may be used by control module 80 for determining a required number of individual pulses, determining individual pulse width and/or determining the capacitance used to produce each individual pulse of the composite pacing pulse in order to produce a composite pacing pulse having an amplitude profile for the duration of the pulse width that successfully captures and paces the heart.

In embodiments in which IMD 14 provides high voltage therapy such as cardioversion/defibrillation shock pulses, therapy delivery module 84 may additionally include high voltage (HV) therapy module 83 including one or more high voltage output capacitors. HV therapy module 83 may be optional and omitted when IMD 14 is provided for delivering pacing pulses without the capability of high voltage therapies. When include, IMD 14 may be configured to detection a shockable rhythm such as ventricular fibrillation or fast ventricular tachycardia. In response to detecting a shockable rhythm, the HV capacitors are charged to a programmed voltage level by a HV charging circuit. The HV charging circuit may include a transformer and be a processor-controlled charging circuit that is controlled by control module 80. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage therapy module 83 to deliver CV/DF shocks using defibrillation electrode 24 and housing 15.

High energy CV/DF shocks are generally on the order of at least 5 Joules and more commonly on the order of 20 Joules or higher. For the sake of comparison, the HV capacitor(s) of the HV therapy module 83, when included, may be charged to an effective voltage greater than 100 V for delivering a cardioversion/defibrillation shock. For example, two or three HV capacitors may be provided in series having an effective capacitance of 148 microfarads in HV therapy module 83. These series capacitors may be charged to develop 750 to 800 V for the series combination in order to deliver shocks having a pulse energy of 5 Joules or more, and more typically 20 Joules or more. In contrast, low voltage pacing pulses delivered using extra-cardiovascular electrodes may be less than 0.1 Joule. The low voltage capacitor(s) charged for delivering a low voltage pacing pulse may have a capacitance that is much less than the HV capacitor, e.g., 6 to 10 microfarads, and may be charged using a state machine to a multiple of the battery charge of power source 90 without using a transformer. If the LV capacitor or capacitor combination is charged to 8 V for a composite pacing pulse amplitude of 8 V and total pulse width of 8 ms the delivered energy is approximately 1 millijoule if the pacing vector impedance is 500 ohms. Composite pacing pulses, delivered by the LV therapy module 85, having an 8 V amplitude and 8 ms pulse width may be in the range of 0.5 to 1.3 milliJoules for a range of pacing loads between 400 ohms and 1000 ohms. The maximum pulse amplitude available from LV therapy module 85 for delivering low voltage composite pacing pulses may be 10 Volts in some examples and may be higher in other examples, for instance not more than 40 Volts or not more than 20 Volts. Pacing pulses delivered using endocardial electrodes or epicardial electrodes may be much lower in energy, on the order of microjoules, e.g., 2 microJoules to 5 microjoules for an endocardial pacing pulse that is 2V in amplitude, 0.5 ms in pulse width and applied across a pacing electrode vector impedance of 400 to 1,000 ohms. An extra-cardiovascular composite pacing pulse may be greater than 100 microjoules and less than 1 Joule, for example.

Sensor module 92 may include additional sensors for monitoring the patient for controlling therapy delivery. For example, sensor module 92 may include an activity sensor, a posture sensor, a heart sound sensor, or other physiological sensor(s) for monitoring the patient and making therapy delivery decisions. In various examples, rate responsive pacing may be provided based on a patient activity signal. The rate of low voltage pacing pulses delivered using extra-cardiovascular electrodes may be adjusted based on the activity signal. A decision to deliver ATP or shock therapy may be based in part on physiological sensor signals in addition to the cardiac electrical signal. As such, ATP pulses may be delivered as LV extra-cardiovascular pacing pulses in response to a therapy delivery decision made by control module 80 using physiological sensor signals from sensor module 92.

Control parameters utilized by control module 80 may be programmed into memory 82 via telemetry module 88. For example, the composite pacing pulse width and pacing pulse amplitude may be programmable parameters. Control module 80 may utilize the programmed pacing pulse width and pacing pulse amplitude for controlling the selection, sequence and charging of LV capacitors included in LV therapy module 85. Telemetry module 88 includes a transceiver and antenna for communicating with external device 40 (shown in FIG. 1) using RF communication as described above. Under the control of control module 80, telemetry module 88 may receive downlink telemetry from and send uplink telemetry to external device 40. IMD 14 may communicate with other implantable devices implanted in the patient using telemetry module 88.

Figure 4A:
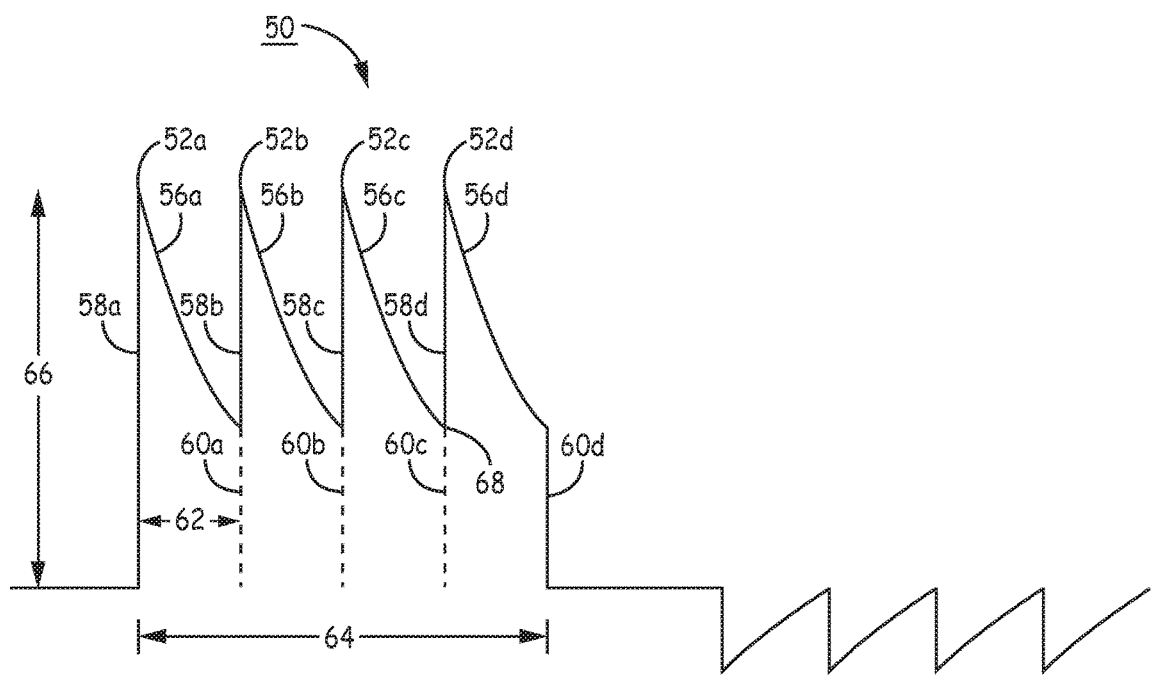
FIG. 4A is a depiction of an example of a composite pacing pulse that may be generated and delivered by the IMD of FIG. 1A to pace a patient's heart using extra-cardiovascular electrodes.

FIG. 4A is a depiction of an example of a composite pacing pulse 50 that may be generated and delivered by IMD 14 to pace heart 26 using extra-cardiovascular electrodes, such as an electrode vector selected from among the electrodes 24A, 24B, 28A, 28B and/or 30 and/or housing 15 shown in FIGS. 1A-2B. In one example, the composite pacing pulses, such as pulse 50 of FIG. 4A and pulse 80 of FIG. 4B described below, are delivered via one of electrodes 28A or 28B as the cathode and the housing 15 as the return anode. In other examples, the composite pulses are delivered using one of electrodes 28A or 28B as the cathode and a defibrillation electrode, such as one of defibrillation electrodes 24A or 24B as the return anode, in examples that include a defibrillation electrode. The techniques for delivering composite pacing pulses disclosed herein, however, are not limited to use with a particular pacing electrode vector.

Composite pacing pulse 50 comprises four pulses 52a, 52b, 52c, and 52d that are each individually delivered by sequentially discharging at least two different holding capacitors (or two different combinations of holding capacitors) across a pacing electrode vector via an output capacitor. The first pulse 52a defines a leading edge 58a of the composite pulse 50. Each of the pulses 52a-52d has a peak voltage amplitude 66 according to a programmed pulse amplitude. A decaying portion 56a, 56b, 56c, and 56d of each individual pulse decays according to an RC time constant of the discharge circuit. Each individual pulse 52a-52d may be truncated at an individual pulse width 62. The leading edge 58b, 58c and 58d of the respective pulses 52b, 52c and 52d coincides in time with the terminating edge 60a, 60b and 60c, respectively of the preceding pulse, 52a, 52b, and 52c, respectively. The terminating edge 60d of the final pulse 52d defines the trailing edge of the composite pulse 50.

The composite pulse 50 has a time-varying pulse amplitude that reaches a peak voltage amplitude 66 at the leading edge 58a-58d of each individual pulse with periods of decay between the leading edges 58a-58d to a minimum pulse amplitude 68 just prior to the next leading edge. The individual pulse width 62 may be set to maintain the minimum pulse amplitude 68 of each individual pulse 52a-52d above a minimum amplitude threshold to ensure that the total pulse energy delivered in the composite pulse 50 successfully captures and paces the heart 26. The individual pulse width 62 may be fixed, e.g., up to 2 ms in some examples so that the total pulse width is up to 8 ms when four fused, consecutive pulses 52a-52b are delivered as shown in the example of FIG. 4A. The individual pulse width may be the maximum individual pulse width that can be produced by LV therapy module 85 when a single low voltage capacitor (or capacitor combination) included in LV therapy module 85 is discharged to deliver an individual pulse. This maximum available pulse width may be based on the effective capacitance of an individual low voltage, holding capacitor (or combination of holding capacitors) and may be a maximum programmable pulse width of an individual pulse.

The number of individual pulses delivered in fused sequence may be selected based on the total pacing pulse width 64 required to capture the heart for a given peak voltage amplitude 66 and the individual pulse width 62. The composite pacing pulse width 64 may be up to 8 ms (as shown), 10 ms, 12 ms, 16 ms, or even 20 ms or more. In some examples, individual pulse width 62 is set to a maximum individual pulse width that can be reached without allowing the minimum pulse amplitude 68 to fall to a minimum amplitude threshold. For example, the minimum pulse amplitude 68 may be prevented from reaching 0 V at terminating edges 60a, 60b, 60c and 60d and may be maintained above an amplitude threshold, which may be defined as a percentage of the programmed peak voltage amplitude 66, e.g., 25%, 50% or other selected percentage of programmed peak voltage amplitude 66.

In other examples, the pacing pulse amplitude may be monitored real time during the delivery of composite pacing pulse 50, and, when the decaying amplitude drops to an amplitude threshold value, the next individual pulse is started. For example, the amplitude of decaying portion 56a may be sampled, and when the minimum amplitude 68 is reached the next pulse 52b is started. The first pulse 52a is truncated when the next pulse 52b is started so that terminating edge 60a of pulse 52a and leading edge 58b of the second pulse 52b occur simultaneously, or nearly simultaneously within the limits of the electronic circuitry. It is recognized that limitations within the electronic circuitry may result in a non-zero time gap between individual pulses 52a-52d in some examples. The delivered energy of each individual pulse 52a-52d, however, is fused close enough in time to a preceding and/or subsequent individual pulse such that the individual pulse energies accumulate to achieve a dose response necessary to achieve capture of the patient's heart. Each individual pulse 52a-52d may have a pulse energy below the capture threshold of the heart. By delivering the individual pulses 52a-52b within a time window defined by the total pulse width 64, the total composite pacing pulse energy that is delivered is greater than the pacing capture threshold of the heart. As such, the composite pulse captures the heart even when each individual pulse 52a-52d, if delivered alone or spaced further apart in time, may be insufficient to capture and pace the heart. In some examples, a pacing capture threshold test may be performed using methods generally disclosed in U.S. Patent. Application No. 62/262,499 and corresponding U.S. Pat. No. 10,080,905, both incorporated herein by reference in their entirety.

Each individual pulse 52a-52d may be delivered across the pacing electrode vector having the same polarity (positive-going in the example shown) by sequentially coupling different capacitance elements across the selected pacing electrode vector. Each of the different capacitance elements are previously charged to the peak voltage amplitude 66 prior to being coupled across the pacing electrode vector. In some examples, the same capacitor or combination of capacitors may not be used to deliver two consecutive individual pulses, e.g., 52a and 52b, since charging of the capacitor (or combination of capacitors) to the peak voltage amplitude 66 occurs prior to initiating each respective one of the individual pulses 52a-52d. The same capacitor or same combination of capacitors may be used to deliver two non-consecutive individual pulses, e.g., 52a and 52d by recharging the same capacitor or combination of capacitors to the peak voltage amplitude 66 during the intervening one or more individual pulses 52b and 52c.

All individual pulses 52a-52d are shown to have the same peak voltage amplitude 66 in FIG. 4A. The peak voltage amplitude may be the maximum voltage amplitude available from the LV therapy module 85 or a maximum voltage amplitude acceptable by the patient. The total pulse energy of the composite pacing pulse 50 is controlled by setting the individual pulse number and individual pulse width of pulses 52a-52d. It is contemplated, however, that one capacitor (or combination of capacitors) that is discharged to deliver one of the individual pulses 52a-52d may be charged to a different voltage than another capacitor (or combination of capacitors) used to deliver a different one of the individual pulses 52a-52d. As a result, the individual pulses 52a-52d may have different peak voltage amplitudes in some instances. Individual pulses 52a-52d, however, are generated by switching out a first discharging capacitor (or combination of capacitors) and switching in a next capacitor (or combination of capacitors) that is(are) charged to the desired peak voltage amplitude of the next individual pulse. A first individual pulse is thereby terminated by stopping discharging of the first capacitor(s), and the next individual pulse is started by starting discharging of the next capacitor(s).

Pacing pulse 50 is followed by a recharge pulse 70 comprising a low amplitude pulse in opposite polarity for each of the individual pulses 52a-52d. The recharge pulse 70 may allow an output capacitor of the LV therapy module 85 to passively discharge if it has charged during the delivery of pacing pulse 50 to promote charge neutrality. The recharge pulse 70 may reduce polarization artifact of the pacing electrodes.

Figure 4B:
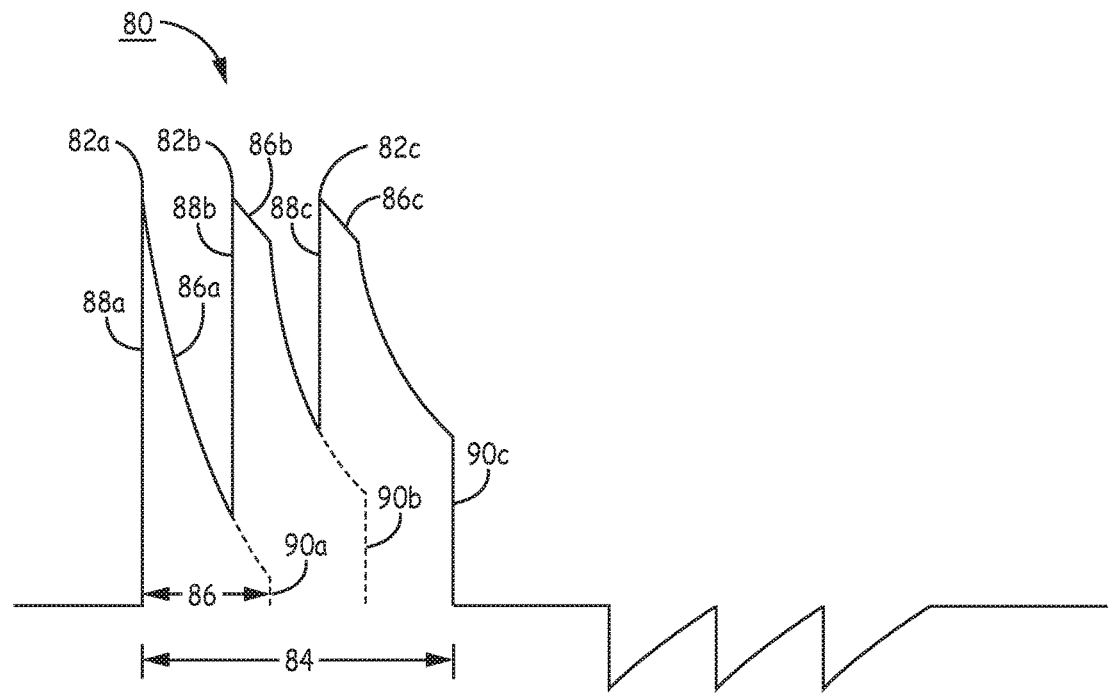
FIG. 4B is a depiction of a composite pacing pulse according to another example.

In FIG. 4A, individual pulses 52a-52d are fused in time but are not overlapping in that the leading and terminating edges of the individual pulses are simultaneous or near simultaneous within the limits of the electronics. In other examples, the individual pulses may be overlapping. FIG. 4B is a depiction of a composite pacing pulse 80 having leading edge 88a and terminating edge 90c according to another example. Pulse 80 includes three overlapping pulses 82a, 82b and 82c. The leading edges 88b and 88c of the second and third pulses 82b and 82c, respectively, occur before the terminating edge 90a and 90b of the respective preceding pulses 82a and 82b. In this case, the decaying portions 86a, 86b and 86c of the individual pulses 82a, 82b and 82c may have differing decay rates due to overlapping portions of pulse 82a and pulse 82b and overlapping portions of pulse 82b and pulse 82c. Electronic circuitry such as one or more diodes may be used to prevent charge distribution between capacitors when an individual pulse 82b or 82c is started prior to truncation of the preceding pulse 82a or 82b, respectively.

Figure 5:
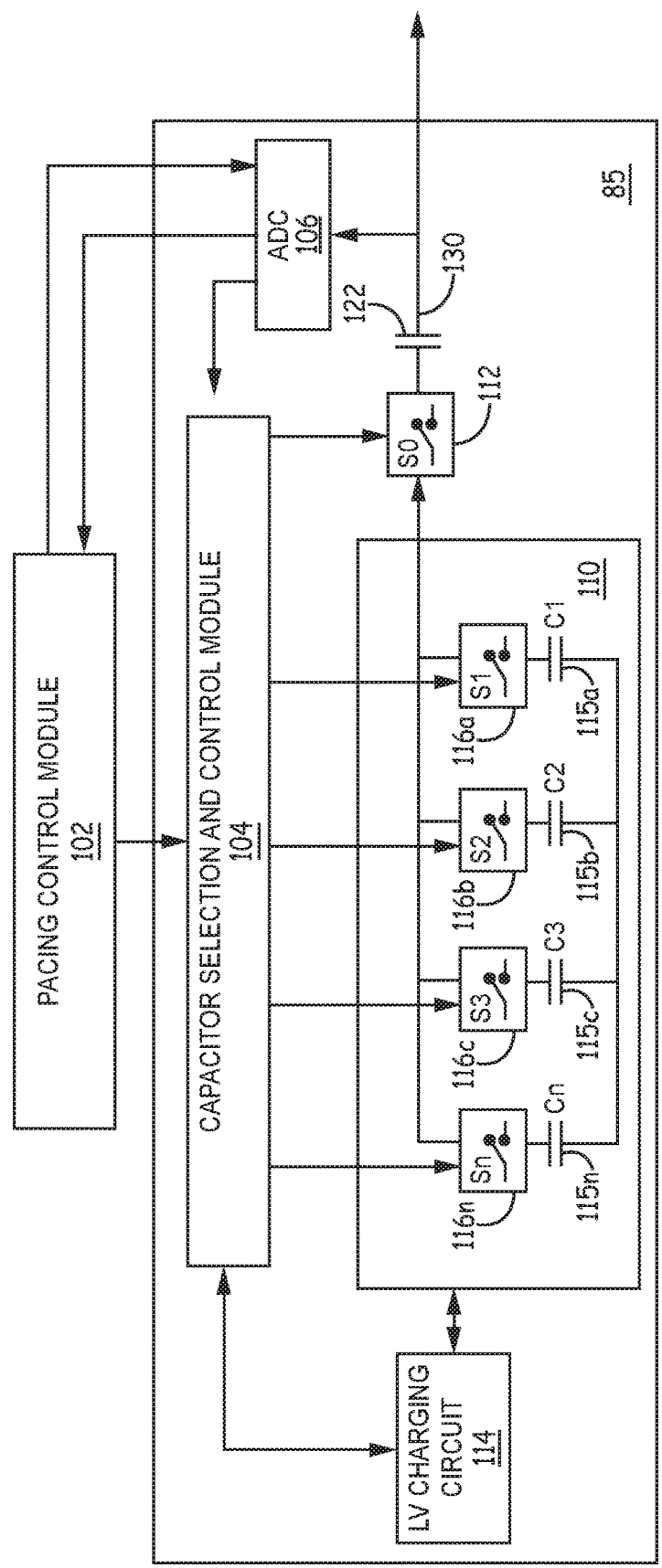
FIG. 5 is a schematic diagram of a pacing control module and a low voltage therapy module according to one example.
Figure 13:
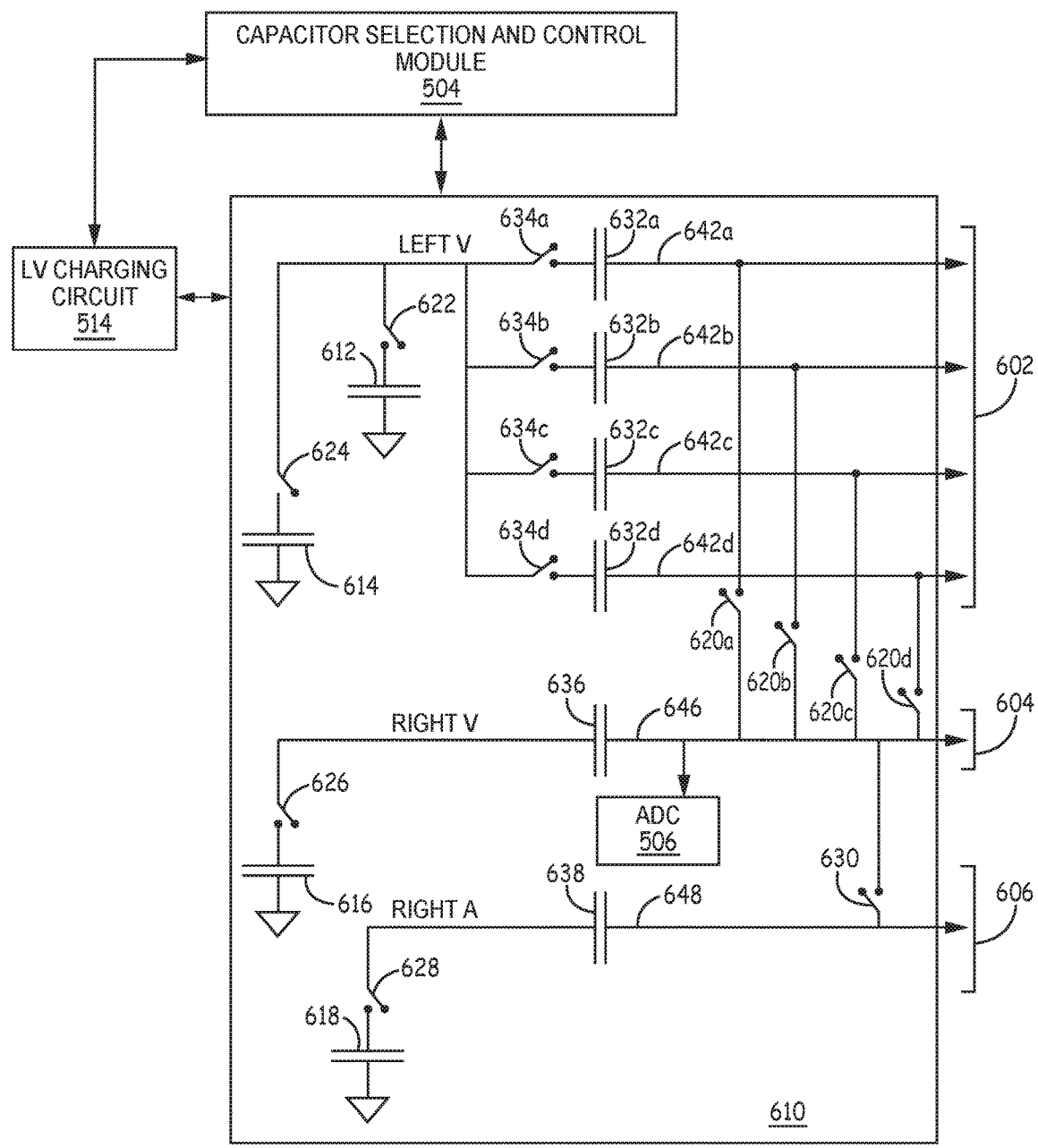
FIG. 13 is a conceptual diagram of low voltage therapy module according to another example.

FIG. 5 is a schematic diagram of a pacing control module 102 included in control module 80 and the LV therapy module 85 included in therapy delivery module 84. LV therapy module 85 includes a capacitor selection and control module 104 and a capacitor array 110. Capacitor array 110 includes multiple holding capacitors 115a through 115n (labeled C1 through Cn, collectively 115), arranged in parallel in this example. Each capacitor C1 through Cn is selectable via a respective one of parallel switches 116a, 116b, 116c through 116n, collectively 116, (labeled S1 through Sn). Switches 116 are controlled by capacitor selection and control module 104 to selectively control which capacitors C1 through Cn 115 are coupled to a pacing pulse output signal line 130 via switch 112 for pacing pulse delivery across output capacitor 122. While output capacitor 122 is represented as a single output capacitor element, it is to be understood that output capacitor 122 may represent multiple output capacitors where one output capacitor may be provided in series with each holding capacitor 115a-115n so that each holding capacitor of array 110 can be discharged across a respective output capacitor to deliver each individual pulse in timed sequence. In this case, each output capacitor may be coupled to a respective holding capacitor 115a-115n via a respective switch that, when closed, enables one or more holding capacitors 115a-115n selected by closure of respective ones of switches 116 to be discharged across the respective output capacitor. A configuration of LV therapy module 85 including multiple output capacitors is shown in FIG. 13.

If output capacitor 122 is provided as a single capacitor as shown, it may be provided with an equivalent capacitance that is selected based on the sum of the capacitances of all of the parallel holding capacitors C1-Cn of array 110 so that the output capacitor 122 does not become charged on the first individual pulse in a way that blocks delivery of subsequent pulses delivered by subsequent discharging of one or more holding capacitors 115. For example, output capacitor 122 may have a capacitance at least equal to the sum of capacitors C1-Cn 115.

Switches 116 may be enabled or closed for the individual pulse width one at a time to couple a respective one of capacitors 115 to output signal line 130 one at a time in a controlled sequence for delivering the fused individual pulses of the composite pacing pulse. In some examples, switches 116 may be enabled or closed in combinations that enable two or more of capacitors 115a through 115n to be coupled to output signal line 130 simultaneously for delivering an individual pulse. When two or more of capacitors 115a through 115n are used in combination to deliver an individual pulse of the composite pulse, the higher effective capacitance results in a longer RC time constant and slower decay of the pulse amplitude during the composite pacing pulse.

While four capacitors are shown, capacitor array 110 may include more or fewer capacitors, which may depend on the requirements of the particular pacing application and available volume in the housing 15. In other examples, capacitor array 110 includes two or three capacitors. In still another example, capacitor array 110 includes five or six capacitors. Capacitors C1 through Cn 115 may be provided with a capacitance of 6 to 10 microfarads in one example, and may have the same or different capacitances, but capacitances greater than or less than this range may be used to provide a desired effective capacitance for delivering each individual pulse. Larger capacitors (or larger effective capacitance of a combination of capacitors) may enable longer individual pulse widths to be used to produce an overall longer composite pacing pulse or a composite pacing pulse comprising fewer individual pulses. C1 through Cn capacitors 115 are shown coupled in parallel. In other examples, some capacitors in array 110 may be coupled in series, e.g., C1 and C2 may be coupled in series and in parallel with C3. Selectable arrangements of the capacitors 115 in parallel and/or in series provides control of the RC time constant of the discharge circuit and the effective capacitance of the discharge circuit including output capacitor 122 and the pacing electrode vector impedance according to a particular pacing application. Various configurations of single, parallel or series capacitors 115 may be selected via switching circuitry included in capacitor array 110 for enabling a desired effective capacitance for delivering an individual pulse of the composite pacing pulse.

Pacing control module 102 provides control signals to capacitor selection and control module 104 to control the timing, pulse amplitude, and pulse width of a composite pacing pulse. The pulse amplitude may be set by pacing control module 102 according to a programmed pulse amplitude, and the pulse width may be controlled according to a programmed pulse width. Pacing control module 102 may determine the capacitor configuration based on the number of fused individual pulses required to achieve the overall pulse width of the composite pacing pulse.

Capacitor selection and control module 104 controls LV charging circuit 114 to charge a selected number of the capacitors C1 through Cn 115 for delivering the composite pacing pulse. For example, three capacitors C1 through C3 may be selected one at a time for delivering a composite pulse comprising three fused pulses; four capacitors C1 through C4 may be selected one at a time for delivering a composite pulse comprising four fused pulses and so on. LV charging circuit 114 charges the selected capacitors to a voltage level according to the programmed pacing pulse amplitude to supply pacing pulse energy. Power source 98 (FIG. 3) may provide regulated power to LV charging circuit 114. LV charging circuitry 114 may be controlled by a state machine to charge the selected capacitors using a multiple of the battery voltage of power source 98, e.g., four times the battery voltage. LV charging circuit 114 may be controlled to charge the selected capacitors simultaneously or sequentially as needed for delivering the series of fused individual pulses.

In response to a timing signal from pacing control module 102, capacitor selection and control module 104 sequentially couples the selected capacitors (or capacitor combinations) one at a time to output signal line 130 via switch 112 to sequentially discharge the selected capacitors (or capacitor combinations) across output capacitor 122 and a pacing electrode vector coupled to output signal line 130. Each capacitor (or combination of capacitors) is discharged for an individual pulse width that is fused in an overlapping or non-overlapping manner with the next individual pulse delivered by discharging the next capacitor (or combination of capacitors) in the sequence. For example, capacitor selection and control module 104 may sequentially enable selected ones of switches 116a through 116n to couple the selected ones of capacitors C1 through Cn 115 to output signal line 130 in a sequential order. The capacitor selection and control module 104 uncouples capacitor array 110 from output signal line 130 by opening switch 112 at the expiration of a programmed composite pacing pulse width (or upon expiration of the last individual pulse width).

In some examples, LV therapy module 85 includes an analog-to-digital converter (ADC) 106 for sampling the pacing pulse output on signal line 130 and providing a digital feedback signal to capacitor selection and control module 104 and/or pacing control module 102. During the pacing pulse, pacing control module 102 enables ADC 106 to sample the pacing pulse output signal on output signal line 130 at a desired sampling rate, e.g., every 2 microseconds, throughout the pacing pulse width. ADC 106 may be enabled to sample the pacing pulse amplitude from the start of the pacing pulse when switch 112 is enabled until the end of the pacing pulse when switch 112 is disabled or a portion thereof.

Pacing control module 102 may monitor the sampled pacing pulse amplitude received from ADC 106 during pacing pulse delivery by comparing the sample points to an amplitude threshold or to an expected amplitude. An expected amplitude may be based on the predicted decay rate of an individual pulse according to a known or estimated RC time constant of the discharge circuit. In one example, the sample points are compared to an amplitude threshold, which may be set as a percentage of the programmed pacing pulse amplitude, e.g., 50% of the programmed pacing pulse amplitude. If the pacing pulse amplitude falls below the amplitude threshold, the pacing control module 102 passes a timing signal to capacitor selection and control module 104 to cause the next individual pulse in the fused series of pulses to begin by switching in the next capacitor (or combination of capacitors) in the array 110 to begin discharging (e.g., by closing the associated switch from among switches S1 through Sn) to maintain the amplitude above a minimum amplitude threshold level throughout the composite pacing pulse width. The preceding individual pulse may continue for a predefined individual pulse width or it may be truncated upon starting the next pulse by disabling the previously enabled capacitor(s) by opening the associated switch(es) from among switches S1 through Sn 116 when the next holding capacitor(s) is/are enabled for discharging the next individual pulse.

Figure 6:
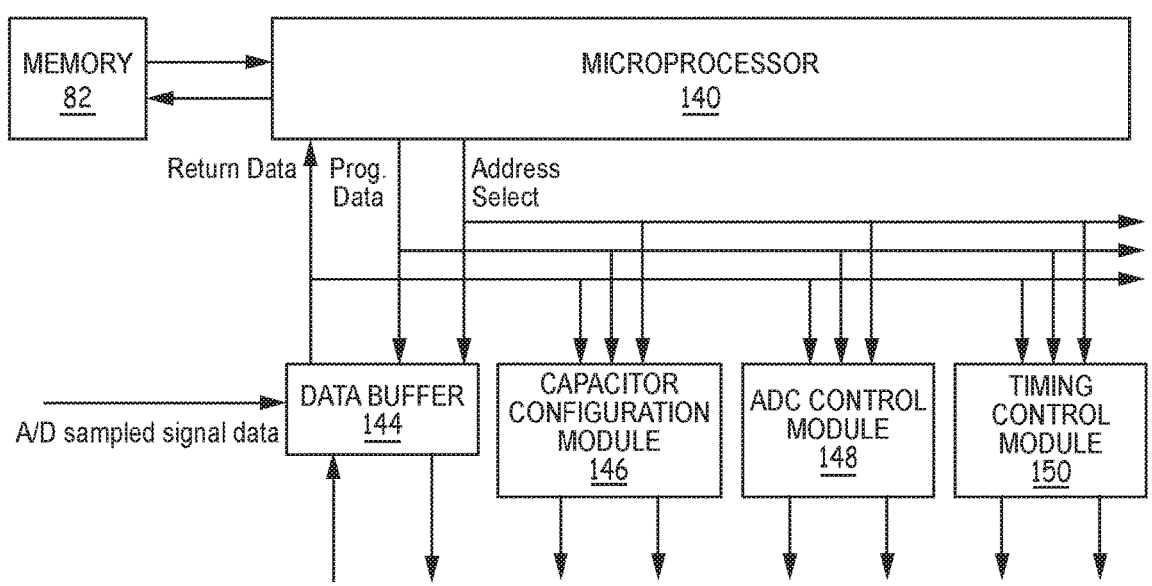
FIG. 6 is a schematic diagram of the pacing control module of FIG. 5 according to one example.

FIG. 6 is a schematic diagram of pacing control module 102 included in control module 80 and capable of accessing instructions stored in memory 82 according to one example. Pacing control module 102 may include a microprocessor 140 that is configured to execute instructions stored in memory 82 for selecting a series of capacitors or combinations of capacitors and setting the pulse amplitude and pulse width for delivering composite pacing pulses.

Microprocessor 140 provides capacitor configuration data to capacitor configuration module 146 which passes the capacitor configuration data to the capacitor selection and control module 104 of LV therapy module 85 (FIG. 3). The capacitor (or combination of capacitors) to be selected for delivering each individual pulse may be passed to capacitor selection and control module 104 one at a time, e.g., on a clock cycle, until all individual pulses have been delivered. In other examples, capacitor configuration module 146 may pass the capacitor configuration data for the entire series of individual pulses and capacitor selection and control module 104 may select the capacitor(s) for each individual pulse in the appropriate, sequential order.

The timing control module 150 may be controlled by microprocessor 140 to pass timing signals to capacitor selection and control module 104 to control the timing of the leading edge of the composite pulse, the leading edges of subsequent pulses, the time of truncation of individual pulses, and the terminating edge of the composite pulse. The individual pulse widths and the overall pulse width of the composite pacing pulse may be predetermined, e.g., stored in memory 82. Microprocessor 140 may control the delivery of the series of fused individual pulses by passing the capacitor selection and timing information for each individual pulse to capacitor selection and control module 104 via capacitor configuration module 146 and timing control module 150.

Microprocessor 140 may also pass instructions to ADC control module 148. ADC control module 148 may be configured to control the sampling rate and sampling intervals over which ADC 106 (FIG. 5) is enabled. Pulse amplitude sample points may be received by data buffer 144 from ADC 106 and passed to microprocessor 140. Microprocessor 140 may be configured to compare the sampled amplitude values to an amplitude threshold. Based on this comparison, microprocessor 140 may determine when the next pulse in the sequence of individual pulses is required and passes a timing signal to timing control module 150. Timing control module 150 in turn passes the timing signal to capacitor selection and control module 104, e.g., on the next clock signal. The capacitor selection and control module 104 responds to the timing signal by switching in the next capacitor(s) in the series of capacitors or capacitor combinations that is scheduled to start the next individual pulse of the series of fused pulses. For example, the next individual pulse in the series of fused pulses may be started when the pulse amplitude falls to an amplitude threshold, below an expected or predicted amplitude based on a known or estimated RC time constant of the discharge circuit, or when a predetermined individual pulse width expires, whichever comes first.

Data buffer 144 may receive impedance data from impedance measurement module 90. Microprocessor 140 may retrieve the impedance measurement data for use in determining the individual pulse width used to deliver fused pulses. The decay rate of an individual pulse will depend on the impedance of the selected pacing electrode vector and the effective capacitance of the individual capacitor or capacitor combination used to deliver the individual pulse. The RC time constant, sometimes referred to as "tau," may be determined using the measured pacing vector impedance and the capacitance of the individual capacitor or capacitor combination to be used for delivering an individual pulse. The voltage amplitude of the individual pulse at truncation may be predicted at different pulse widths based on the RC time constant. The individual pulse width may be set to a value that results in a predicted voltage amplitude at the terminating edge of the individual pulse that is greater than an amplitude threshold.

Timing control module 150 receives pacing pulse timing data from microprocessor 140, which may include the starting time and/or pulse width of each individual pulse. The time to start the first pacing pulse and the pulse width of the individual pulses are passed to capacitor selection and control module 104. The pulse width of the first pulse may be applied to all individual pulses in the composite pulse such that upon expiration of the individual pulse width, the nth pulse is truncated and the n+1 pulse is started and an individual pulse width timer restarted. If the next pulse in the series of pulses is started prior to truncation of the preceding pulse, in a fused overlapping manner as shown in FIG. 4B, the time to start the leading edge of the next pulse is also passed from timing control module 150 to capacitor selection and control module 104. In other examples, different individual pulse widths may be used such that timer control module passes individual pulse widths for each pulse in the series. A composite pacing pulse having differing individual fused pulse widths is described below in conjunction with FIG. 14.

Figure 7:
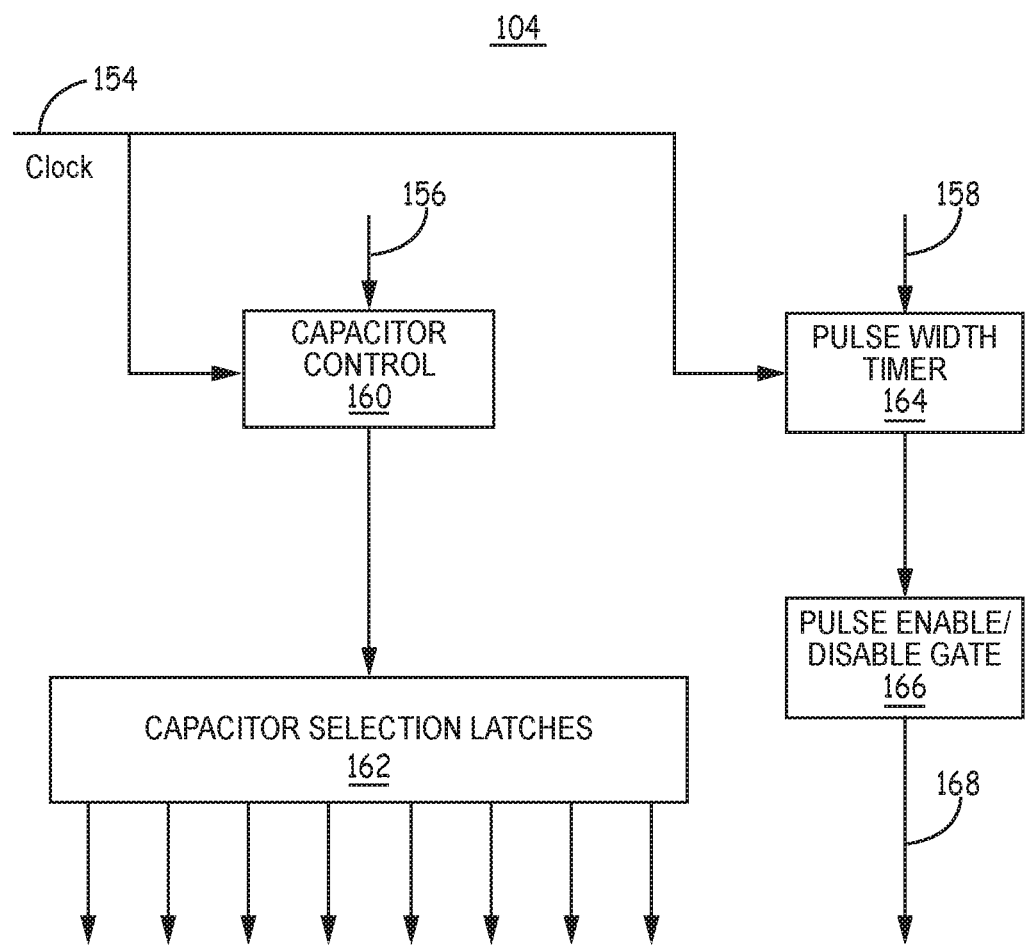
FIG. 7 is a schematic diagram of a capacitor selection and control module according to one example.

FIG. 7 is a schematic diagram of capacitor selection and control module 104 included in LV therapy module 85 according to one example. Capacitor selection and control module 104 includes a capacitor control 160, capacitor selection latches 162, pulse width timer 164 and pacing pulse enable/disable gate 166. Capacitor control 160 receives a clock signal 154 and an input signal 156 from capacitor configuration control module 146 of pacing control module 102 (FIG. 6). The input signal 156 includes capacitor selection data indicating the capacitor(s) that are to be selected for each individual pulse of the composite pacing pulse.

Capacitor control 160 clocks the capacitor configuration data to capacitor selection latches 162, which store the configuration data until passed to the S1-Sn switches 116 of the capacitor array 110 (FIG. 5). In accordance with the configuration data, capacitor selection latches 162 set separate signals that are passed to each of the respective switches S1-Sn 116 to selectively enable or disable each one of capacitors C1 through Cn 115 as needed for each individual pulse delivery. The capacitor selection latches 162 are controlled by capacitor control 160 to sequentially select individual capacitors or capacitor combinations to deliver the series of fused pulses.

Pulse width timer 164 receives clock signal 154 and input from timing control module 150 (FIG. 6) on signal line 158. Pulse width timer 164 passes a timing control signal to pulse enable/disable gate 166. For example, upon expiration of a pacing escape interval, timing control module 150 passes a signal to pulse width timer 164 to enable LV therapy module 85 to start a pacing pulse. Pulse enable/disable signal gate 166 outputs a signal on signal line 168 to switch 112 (FIG. 5) to start the pacing pulse. Switch 112 is controlled by gate 166 to couple the first selected capacitor or combination of capacitors to pacing pulse output signal line 130 for the first individual pulse. Switch 112 remains enabled or closed for the composite pacing pulse width under the control of pulse enable/disable gate 166. Pulse width timer 164 may be set to the composite pulse width so that pulse enable/disable gate 166 disables or opens switch 112 upon expiration of the composite pacing pulse width to uncouple the capacitor array 110 from the output signal line 130.

In some examples, capacitor control 160 and pulse width timer 164 receive capacitor and timing data from pacing control module 102 on signal lines 156 and 158 on an individual pulse-by-pulse basis. Pulse width timer 164 may enable switch 112 for the duration of the composite pacing pulse width. During the composite pacing pulse width, pulse width timer 164 may set an individual pulse width timer for controlling the times that capacitor selection and control module 104 enables/disables individual switches S1 through Sn 115 according to the capacitor selection for each individual pulse. Pulse width timer 164 may include one or more individual pulse timers for controlling the termination time of individual pulses and the timing of the leading edge of the next pulse. Upon the expiration of each individual pulse width, capacitor control 160 controls capacitor selection latches 162 to select the next capacitor or capacitor combination for starting the next individual pulse according to data received on signal line 156. Capacitor control 160 may receive data indicating the capacitor(s) to be used for each individual pulse in a serial manner on signal line 156 and consecutively select the capacitor selections via latches 162.

Alternatively, all capacitor selection data representing the desired number of individual pulses and capacitor selections for delivering the entire composite pacing pulse may be passed to capacitor control 160 on a single pass. Capacitor control 160 sequentially controls latches 162 to step through the individual capacitor selections as each individual pulse width expires according to timing signals from timer 164.

In some examples, pacing control module 102 receives the sampled pacing pulse signal amplitude and compares the sampled amplitude to an amplitude threshold. For example, if the pacing pulse amplitude falls to an amplitude threshold before the start of the next individual pulse or expiration of the composite pulse width, the next capacitor selection for the next individual pulse may be triggered.

Upon expiration of the composite pacing pulse width, pulse width timer 164 passes a pulse termination signal to pulse enable/disable gate 166 that outputs a signal on control signal line 168 that terminates the pacing pulse by disabling switch 112 to uncouple the capacitor array 110 from output signal line 130.

Figure 8:
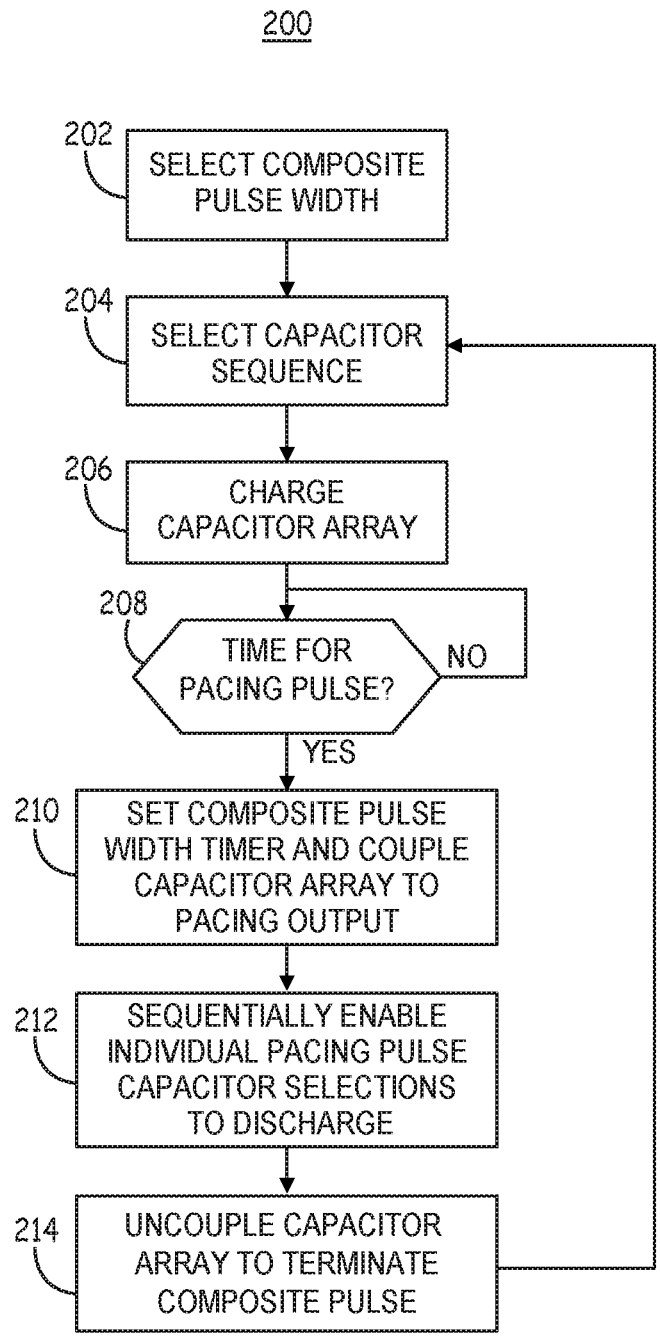
FIG. 8 is a flow chart of a method for delivering extra-cardiovascular pacing pulses according to one example.

FIG. 8 is a flow chart 200 of a method for delivering extra-cardiovascular pacing pulses by IMD 10 according to one example. At block 202, the composite pacing pulse width is selected. The pacing pulse width may be selected based on capture threshold tests. For example, using a default pacing pulse amplitude or a pacing pulse amplitude selected to be below a discomfort level of the patient, the minimum pacing pulse width required to capture (successfully pace) the heart may be determined. The pacing pulse width of the composite pacing pulse may be set to a safety interval longer than the capture pulse width threshold to reduce the likelihood of loss of capture.

At block 204 the capacitor sequence for delivering the composite pulse is selected. In one example, the pacing pulse width set at block 202 is divided by a predetermined individual pulse width to determine the number of fused individual pulses having equal pulse widths that is required to meet or exceed the composite pacing pulse width. For example, if the pulse width capture threshold is 2.5 ms, the composite pacing pulse width may be set to 3 ms at block 202. The predetermined individual pulse width may be set to 1 ms so that three fused pulses are required to achieve the 3 ms composite pacing pulse width. The capacitor sequence selected at block 204 is three capacitors, e.g., C1, C2 and C3, to be enabled in sequential order for discharging across the pacing vector, each for 1 MS.

In another example, if the composite pacing pulse width is set to 2 ms, the pacing control module 102 may select the capacitor sequence as the combination of C1 and C2 for delivering the first individual pulse of 1 ms and the combination of C3 and C4 to deliver the second individual pulse of 1 ms. In yet another example, if the pacing pulse width is set to 7.5 ms, a sequence of C1-C2-C3-C4-C1 may be selected such that each individual capacitor is enabled one at a time in sequence to discharge for a 1.5 ms individual pulse width, and C1 may be recharged after the first individual pulse during the delivery of the second through fourth individual pulses so that it is enabled to deliver the fifth individual pulse. The five sequential 1.5 ms pulses are fused in a non-overlapping manner such that a 7.5 ms pacing pulse is delivered.

A maximum composite pacing pulse width may be up to 10 ms or more in various examples. The maximum individual pulse width may be set based on the capacitance of the individual capacitor or combination of capacitors being used. For example, the maximum individual pulse width may be 2 ms, 4 ms or other predetermined value for a given effective capacitance used to deliver the individual pulse.

The capacitors 115 of array 110 may be selected singly for delivering each individual pulse of the composite pulse or in combinations of two or more at a time for delivering each individual pulse. Numerous sequential orders of enabling the capacitor(s) selected for delivering each individual pulse may be conceived. Furthermore, a selected sequence may involve one or more capacitors that are discharged, recharged and discharged again to deliver more than one of the individual pulses during a single composite pacing pulse.

The capacitors selected for delivering the composite pacing pulse are charged by LV charging circuit 114 at block 206 under the control of capacitor selection and control module 104. All capacitors that are being utilized to deliver the pacing pulse may be charged simultaneously to the programmed pacing pulse voltage amplitude. In other examples, the capacitors may be charged in a sequential order according to the order in which they will be discharged during pacing pulse delivery. When a capacitor or capacitor combination is being used more than once during a composite pacing pulse, LV charging circuit 114 recharges the capacitor (or capacitor combination) while another capacitor or capacitor combination is being discharged to deliver an individual pulse. LV charging circuit 114 may include capacitor charge pumps or an amplifier for the charge source to enable rapid recharging of holding capacitors included in capacitor array 110.

At block 208, pacing control module 102 determines if it is time for delivering a pacing pulse. This determination may be made based on the expiration of a pacing interval. The pacing interval may be, for example and with no limitation intended, a V-V pacing escape interval such as a lower rate interval for bradycardia pacing, a back-up escape interval for pacing during asystole or post-shock pacing, or an ATP interval during delivery of ATP. The pacing interval may alternatively be an interval used to deliver entrainment pacing pulses prior to T-shock delivery for tachyarrhythmia induction or a 50 Hz burst interval for tachyarrhythmia induction. Pacing control module 102 may wait for a pacing escape interval to expire at block 208, and, when it expires, timing control module 150 passes a signal to capacitor selection and control module 104 to start a composite pacing pulse.

Capacitor selection and control module 104 may set a composite pulse width timer included in pulse width timer 164 at block 210 and couples the capacitor array 110 to pacing output signal line 130, e.g., by enabling or closing switch 112 of FIG. 5. At block 212, capacitor selection and control module 104 sequentially enables the capacitor(s) selected for delivering each individual pulse according to data received from capacitor configuration module 146 (FIG. 6). Each capacitor or combination of capacitors in the series is enabled by closing respective switch(es) S1-Sn 116 for the individual pulse width to discharge the selected capacitor(s) across the pacing electrode vector. A single capacitor or combination of capacitors is selected as a capacitance element that is discharged for delivering of an individual pulse of the composite pacing pulse. Pacing control module 102 selects a sequence of capacitance elements from the capacitors of the capacitor array 110 and a respective individual pulse width for each capacitance element of the sequence so that a sum of the individual pulse widths is equal to or greater than a selected composite pacing pulse width, which is equal to or greater than a pacing pulse width capture threshold for the pacing pulse voltage amplitude being used.

Upon completion of the sequence of fused pulses at the expiration of the composite pacing pulse width, capacitor selection and control module 104 uncouples capacitor array 110 from the pacing output signal line 130 at block 214, and the composite pacing pulse is complete. The composite pacing pulse is delivered to evoke a single depolarization of a heart chamber, e.g., a ventricular heart chamber, to cause a single mechanical contraction or beat of the heart chamber. The leading edge pulse amplitude of each individual pulse and the composite pulse width are selected so that the cumulative delivered energy of the fused individual pulses meets or exceeds the pacing capture threshold using the extra-cardiovascular pacing electrode vector selected to pace the heart. Each individual pulse of the composite pulse may have a pulse energy below the capture threshold but the combined individual pulse energies accumulate during the composite pulse width to reach the pacing capture threshold to cause an evoked response.

Figure 9:
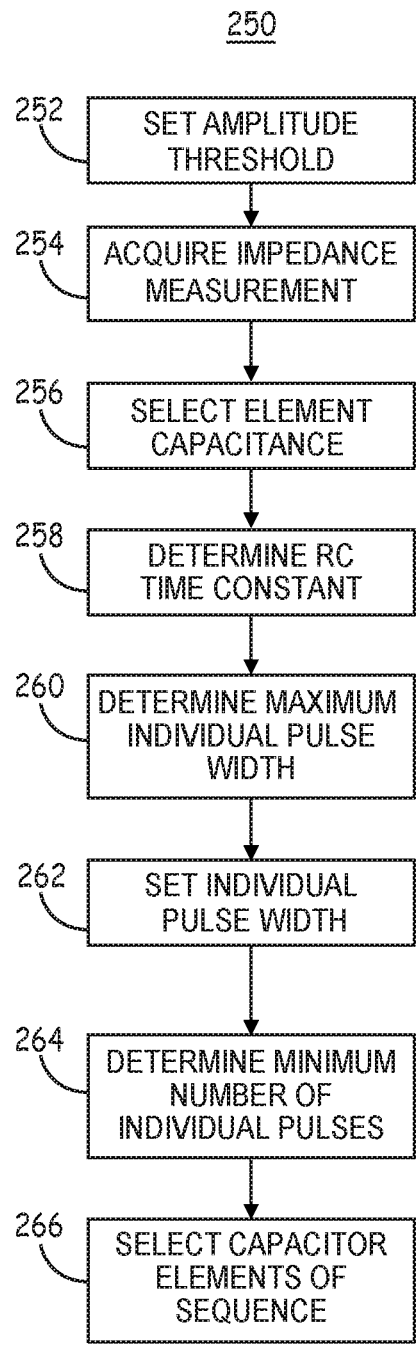
FIG. 9 is a flow chart of a method that may be performed for selecting a capacitor sequence for delivering a composite pacing pulse.

FIG. 9 is a flow chart 250 of a method that may be performed by IMD 14 for selecting a capacitor sequence, e.g., at block 204 of FIG. 8. At block 252, the pacing control module 102 sets an amplitude threshold. The amplitude threshold may be at or above a minimum acceptable voltage of the decaying individual pulses included in the composite pacing pulse. The amplitude threshold may be set based on the programmed pacing pulse amplitude, e.g., 50% of the programmed pacing pulse amplitude. At block 254, the pacing control module 102 acquires an impedance measurement of the pacing electrode vector. Control module 80 may control impedance measurement module 90 to perform an impedance measurement of the pacing electrode vector, or pacing control module 102 may retrieve a previous impedance measurement stored in memory 82.

At block 256, the pacing control module 102 selects an element capacitance. The element capacitance is the effective capacitance of a single capacitor or a combination of two or more capacitors of capacitor array 110 that may be selected simultaneously in series and/or in parallel for delivering an individual pulse of the composite pacing pulse. In some examples, the element capacitance selected at block 256 is the capacitance of a single holding capacitor 115$a$, 115$b$, 115$c$ or 115$n$ in capacitor array 110 or the effective capacitance of a single holding capacitor 115$a$-115$n$ and a respective output capacitor 122. In other examples the element capacitance selected at block 256 depends on the impedance measurement. If the pacing electrode vector impedance measurement is relatively low, a higher element capacitance may be selected, e.g., two of capacitors 115 in parallel. If the pacing electrode vector impedance is relatively high, pacing control module 102 may select an element capacitance of a single capacitor of capacitors 115.

At block 258, pacing control module 102 determines the RC time constant for the measured pacing electrode vector impedance and selected element capacitance. Based on the RC time constant, the pacing control module 102 may predict a maximum possible individual pulse width that could be delivered without the pulse amplitude falling below the amplitude threshold at the terminating edge of the individual pulse, before the leading edge of the next pulse in the sequence. For example, the maximum individual pulse width may be estimated as the time expected for the individual pulse to decay from the programmed pacing pulse amplitude at the pulse leading edge to the amplitude threshold based on the RC time constant. At block 260, the maximum possible individual pulse width is determined for each element capacitance for the series of individual pacing pulses. Pacing control module 102 may set the actual individual pulse width for each individual pulse at block 262 to the maximum possible individual pulse width or less than the maximum possible individual pulse width.

At block 264, pacing control module 102 determines the number of individual pulses at the individual pulse width that are required to at least reach the composite pacing pulse width. For example, if the composite pacing pulse width is set to 4 ms, and the individual pulse width is set to 1 ms at block 262 based on the RC time constant, four fused pulses are required. If the individual pulse width is set to 0.75 ms, the minimum number of pulses may be determined to be 6 pulses which produce a total individual pulse duration of 4.5 ms, longer than the composite pacing pulse width. At block 214 of FIG. 8, the capacitor array 110 may be uncoupled from the pacing output signal line 130 at 4.0 ms, truncating the last individual pulse 0.25 ms after its leading edge. In other examples, capacitor array 110 may be uncoupled from the pacing output signal line 130 after all individual pulses are delivered for the full individual pulse width such that the composite pacing pulse width is exceeded by a portion of an individual pulse width in some cases.

At block 266, the capacitor elements of the capacitor sequence are selected based on the number of individual pulses required and the element capacitance. To illustrate, if the minimum number of individual pulses was determined to be four based on the element capacitance of 10 microfarads (each capacitor C1 through Cn being 10 microfarad capacitors), the capacitor element sequence may be selected as C1-C2-C3-C4 at block 266. If only three capacitors are available, the capacitor sequence may be selected as C1-C2-C3-C1. If the element capacitance is selected as twice 10 microfarads for delivering two fused pulses each of 4 ms long for a composite pulse width of 8 ms, the capacitor elements of the sequence may be selected as C1 in parallel with C2 for the first element and C3 in parallel with C4 for the second element at block 266. After selecting the capacitor elements of the capacitor sequence at block 266, the capacitors included in the sequence may be charged at block 206 of FIG. 8 in preparation for delivering the pacing pulse.

In some cases a relatively larger effective capacitance may be selected for the first individual pulse, either as a single larger capacitor or a combination of capacitors, to ensure that the decay rate of the first pulse is not faster than expected based on feedback from ADC 106. Subsequent capacitance elements may be selected in real-time by pacing control module 102 based on the decay rate of the first pulse. If the decay rate is faster than expected, subsequent capacitance elements may be selected to have an equal or higher effective capacitance than the first capacitance element. If the first pulse does not decay faster than expected, remaining individual pulses may be delivered with a lower effective capacitance than the first pulse. A larger capacitance element may be selected for the first individual pulse as a single holding capacitor when one capacitor, e.g., C1 115*a*, has a larger capacitance than the other capacitors C2-Cn 115*b*-115*n*. Alternatively, a larger capacitance element may be selected for the first individual pulse by selecting two or more individual holding capacitors in parallel, for example C1 115*a* and C2 115*b* in parallel.

Figure 10:
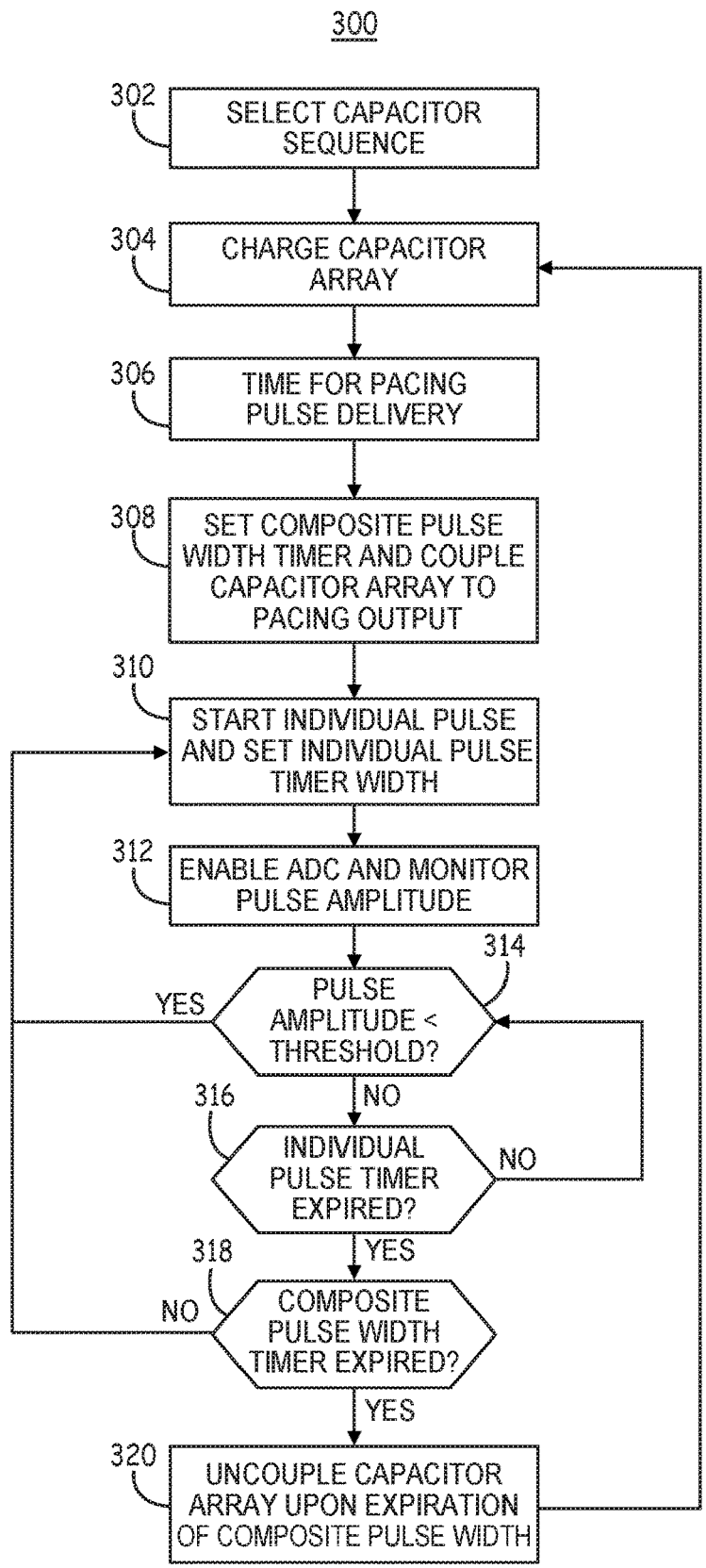
FIG. 10 is a flow chart of a method for delivering a composite pacing pulse according to another example.

FIG. 10 is a flow chart 300 of a method for delivering a composite pacing pulse according to another example. At block 302, a capacitor sequence is selected. The capacitor sequence includes capacitor elements (one capacitor or a combination of capacitors) that are selected in a sequential order for delivering the sequence of individual pulses. The capacitor sequence may be selected according to the methods described in conjunction with FIGS. 8 and 9 or may be predefined.

At block 304, the capacitor array 110 is charged according to a programmed pacing pulse amplitude. At block 306, the pacing control module 102 passes a timing signal to capacitor selection and control module 104 at the time pacing pulse delivery is needed. At block 308, the capacitor selection and control module 104 sets the composite pulse width timer and couples the capacitor array 110 to the pacing output signal line 130 for the composite pacing pulse width.

At block 310, an individual pulse is started by enabling the first capacitor element of the capacitor sequence by closing associated switch(es) 116 to allow the first capacitor element to discharge across the pacing electrode vector. During the pulse, the pacing control module 102 may enable ADC 106 to monitor the pulse amplitude at block 312. Pacing control module 102 receives the sampled voltage signals and compares them to an amplitude threshold at block 314. Pacing control module 102 may establish the amplitude threshold based on the programmed pulse amplitude, e.g., 50% or another percentage of the programmed pulse amplitude. If the sampled pulse amplitude is less than the amplitude threshold at block 314, the next individual pulse is started at block 310.

If the sampled pulse amplitude remains above the threshold at block 314 and the individual pulse width timer expires at block 316, the next individual pulse is started at block 310 by selecting the next capacitor element in the sequence. The pulse amplitude may continue to be sampled and monitored as long as the pulse amplitude remains above the amplitude threshold, until the individual pulse width expires at block 316. If the individual pulse width timer expires at block 316, and the composite pulse width timer has not expired (block 318), the next individual pulse is started at block 310. If the composite pulse width timer has expired, the capacitor array 110 is uncoupled from the output signal line 130 at block 320, and the delivery of the pacing pulse is complete. The process may return to block 304 to charge the capacitors 115 and wait for the time the next pacing pulse is needed at block 306.

In some examples, expiration of the composite pulse width timer at any time during an individual pulse (e.g., before expiration of the individual pulse width timer) may cause truncation of the last pulse before expiration of the individual pulse width timer. In other instances, upon expiration of the composite pulse width timer, the individual pulse being delivered may be allowed to continue until the individual pulse width expires, which may be after expiration of the composite pulse width timer. Using the method of FIG. 10, the number of pulses in the composite pulse and/or the individual pulse width may or may not be predetermined by pacing control module 102. The pacing control module 102 may cause the capacitor selection and control module 104 to enable the next capacitor element of a sequence to start the next individual pulse (n+1) when the sampled pulse amplitude of the current pulse (nth pulse) falls to or below an amplitude threshold. Individual pulses may continue to be delivered in this manner until the composite pulse width timer expires without determining the number of fused pulses in advance of delivering the composite pacing pulse. In this case, the capacitor sequence selected at block 302 may include a sequence of capacitor elements that may be used to deliver up to a maximum number of individual pulses, e.g., 10 pulses, but not all of the capacitor elements in the sequence may be used to deliver pulses if the composite pulse width timer expires before the maximum number of individual pulses is reached.

Figure 11:
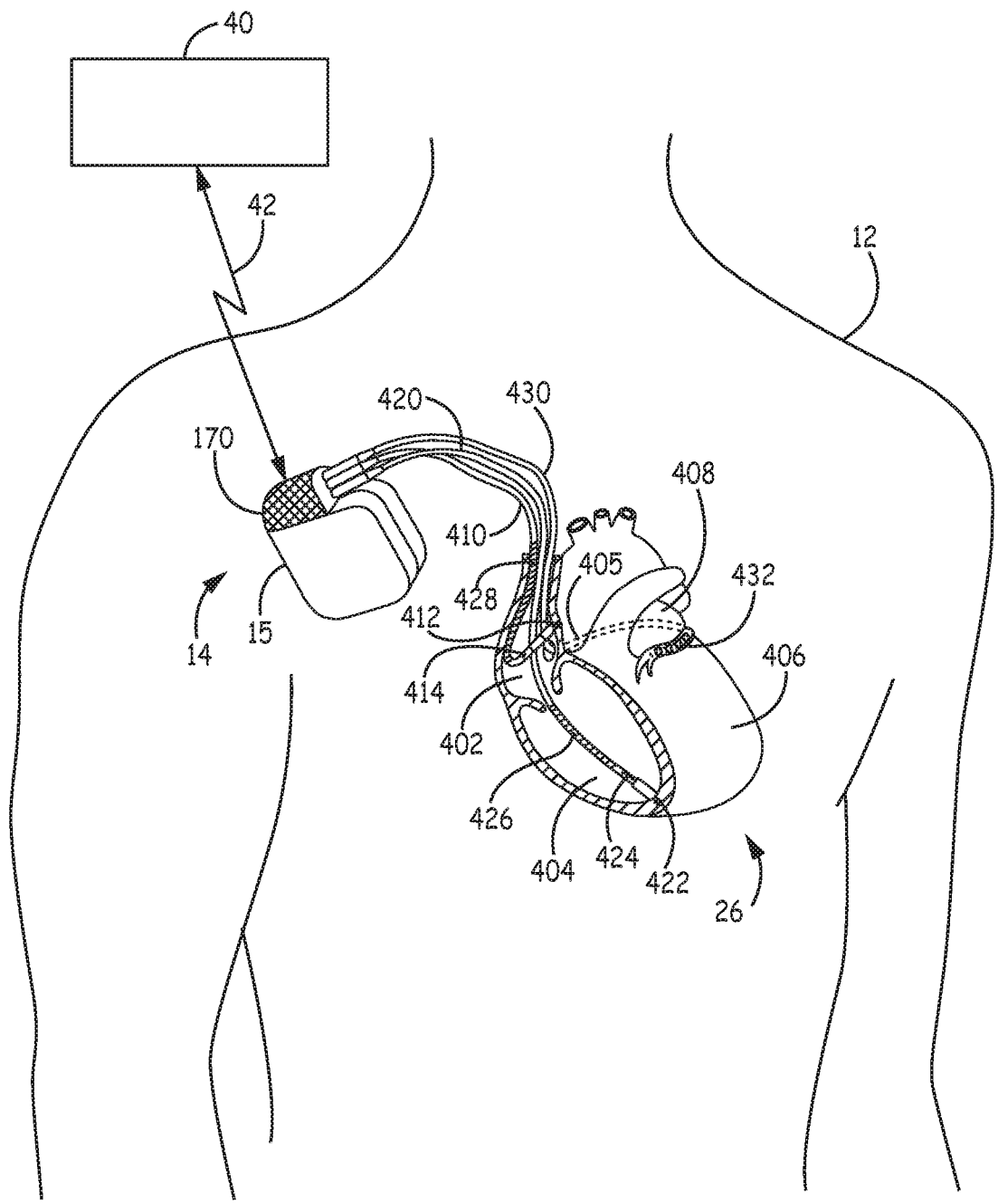
FIG. 11 is a conceptual diagram of an IMD coupled to transvenous leads.

FIG. 11 is a conceptual diagram of IMD 14 coupled to transvenous leads in communication with the right atrium (RA) 402, right ventricle (RV) 404 and left ventricle 406 of heart 26. In some examples, IMD 14 is a multi-purpose device that can be programmably configured to operate as a multi-chamber pacemaker and defibrillator when coupled to transvenous leads 410, 420 and 430 or as an extra-cardiovascular pacemaker and defibrillator when coupled to one or more extra-cardiovascular lead(s), e.g., lead 16 as shown in FIGS. 1A-2B. IMD 14 is shown implanted in a right pectoral position in FIG. 11; however it is recognized that IMD 14 may be implanted in a left pectoral position, particularly when IMD 14 includes cardioversion and defibrillation capabilities using housing 15 as an electrode.

In the example of FIG. 1A, IMD 14 may have a connector assembly 17 having a single connector bore for receiving extra-cardiovascular lead 16. In the configuration of FIG. 11, IMD 14 includes connector assembly 170 having three connector bores for receiving proximal connectors of right atrial (RA) lead 410, right ventricular (RV) lead 420, and coronary sinus (CS) lead 430 to enable IMD 14 to deliver multi-chamber pacing to heart 26. RA lead 410 may carry a distal tip electrode 412 and ring electrode 414 for obtaining atrial intra-cardiac electrogram (EGM) signals and delivering RA pacing pulses. RV lead 420 may carry pacing and sensing electrodes 422 and 424 for obtaining an RV EGM signal and delivering RV pacing pulses. RV lead 420 may also carry RV defibrillation electrode 426 and a superior vena cava (SVC) defibrillation electrode 428. Defibrillation electrodes 426 and 428 are shown as coil electrodes spaced apart proximally from the distal pacing and sensing electrodes 422 and 424.

CS lead 430 is shown as a quadripolar lead carrying four electrodes 432 that may be positioned along a cardiac vein 405. CS lead 430 may be advanced through the coronary sinus into a cardiac vein 405 to position electrodes 432 along the left ventricular lateral wall for obtaining a left ventricular EGM signal and for delivering pacing pulses to the left ventricle. In other examples, one or more electrodes carried by CS lead 430 may be positioned along left atrium 408 for obtaining left atrial EGM signals and/or pacing the left atrium 408.

IMD 14 may be configured to provide dual chamber or multi-chamber pacing therapies, including CRT, using the electrodes 412, 414, 422, 424 and 432 of transvenous leads 410, 420 and 430. IMD 14 may also be capable of detecting and discriminating cardiac tachyarrhythmias and delivering CV/DF shocks as needed using defibrillation electrodes 426 and 428.

Figure 12A:
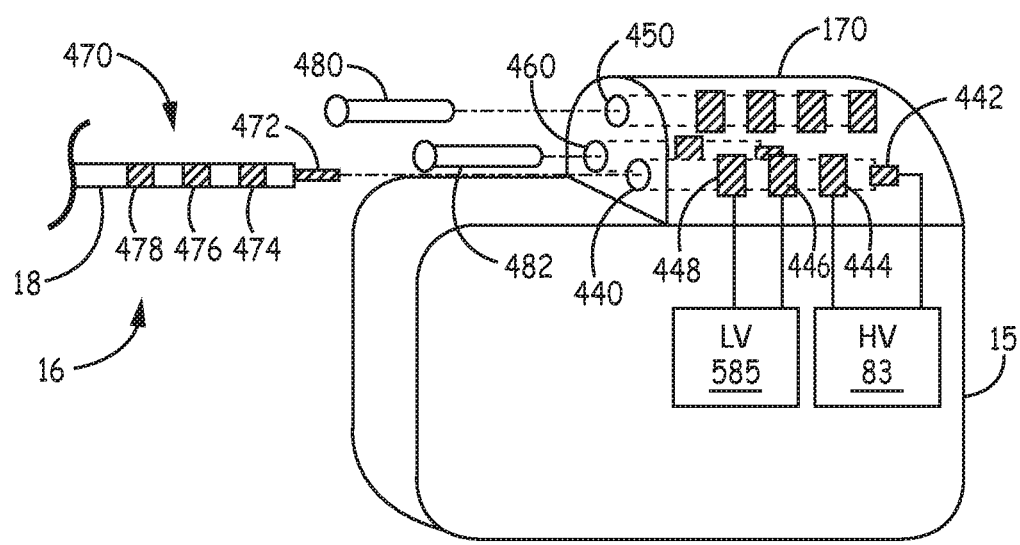
FIG. 12A is a conceptual diagram of the IMD of FIG. 11 and a proximal portion of an extra-cardiovascular lead.

FIG. 12A is a conceptual diagram of IMD 14 and a proximal portion of extra-cardiovascular lead 16 of FIG. 2A or 2B. IMD connector assembly 170 includes three connector bores 440, 450 and 460. Connector bore 440 may include four electrical contacts 442, 444, 446 and 448 and may conform to the DF-4 industry standard. The electrical contacts 442, 444, 446 and 448 are electrically coupled to electronics enclosed within housing 15 via electrical feedthroughs extending from connector assembly 170 into housing 15.

Extra-cardiovascular lead 16 includes a proximal lead connector 470 which may be a quadripolar, in-line connector and may conform to the DF-4 industry standard. Lead connector 470 is configured to mate with connector bore 440 and may include a pin terminal 472 and three ring terminals 474, 476 and 478, which are configured to mate with corresponding contacts 442, 444, 446, and 448, respectively, aligned along connector bore 440. Contacts 442 and 444 may be coupled to HV therapy module 83 and are therefore HV contacts which become electrically coupled to at least one defibrillation electrode carried by lead 16, e.g., electrodes 24A and 24B shown in FIG. 2A or electrodes 24A' and 24B' shown in FIG. 2B.

Ring terminals 476 and 478 of lead connector 470 may each be coupled to pacing and sensing electrodes 28A and 28B (or 28A' and 28B') of lead 16 via necessary conductors (not shown) extending through lead body 18 (or 18'). Ring terminals 476 and 478 are configured to mate with respective contacts 446 and 448 of connector bore 440 so that electrodes 28A and 28B (or 28A' and 28B') are electrically coupled to LV therapy module 585 via terminals 476 and 478 and contacts 446 and 448. As described below in conjunction with FIG. 13, LV therapy module 585 is programmably configurable to either operate to deliver composite pacing pulses for extra-cardiovascular pacing when IMD 14 is coupled to an extra-cardiovascular lead 16 or to operate to deliver multi-channel, multi-chamber pacing when IMD 14 is coupled to a set of transvenous leads such as leads 410, 420 and 430. While not shown in FIG. 12A, it is understood that additional connections may exist as needed between contacts 442, 444, 446 and 448 and other circuitry within housing 15, such as electrical sensing module 86 and impedance measurement module 90 (both shown in FIG. 3) and for coupling all electrodes 24A, 24B, 28A and 28B to LV therapy module 585 so that a pacing electrode vector may be selected from any combination of electrodes 24A, 24B, 28A and 28B (or 28A' and 28B') and/or housing 15.

When IMD 14 is coupled to extra-cardiovascular lead 16, bores 450 and 460 may be unused. These bores 450 and 460 may be sealed with plugs 480 and 482. As described below, IMD 14 may automatically configure LV therapy module 585 for delivering low voltage composite pacing pulses via contacts 442, 444, 446 and/or 448 by coupling capacitor array 110 to contacts 442, 444, 446 and/or 448 in a manner that allows selected capacitors or combinations of capacitors to be sequentially coupled to 442, 444, 446 and/or 448 and discharged across a pacing vector selected from among pacing electrodes 24A, 24B, 28A and 28B (or 28A' and 28B') and/or housing 15. In some examples, electrical contacts 442 and 444 of connector bore 440 may also be coupled to LV therapy module 585 so that defibrillation electrodes or defibrillation electrode segments carried by lead 16 may be selected in a pacing electrode vector for delivery of extra-cardiovascular pacing pulses produced by LV therapy module 585. For example, a pacing electrode vector may be selected to include pace/sense electrode 28A or 28B (or 28A' or 28B') as the pacing cathode and a defibrillation electrode 24A or defibrillation electrode 24B (or 24A' or 24B') as shown in FIG. 2A (or FIG. 2B) as the return anode electrode.

Figure 12B:
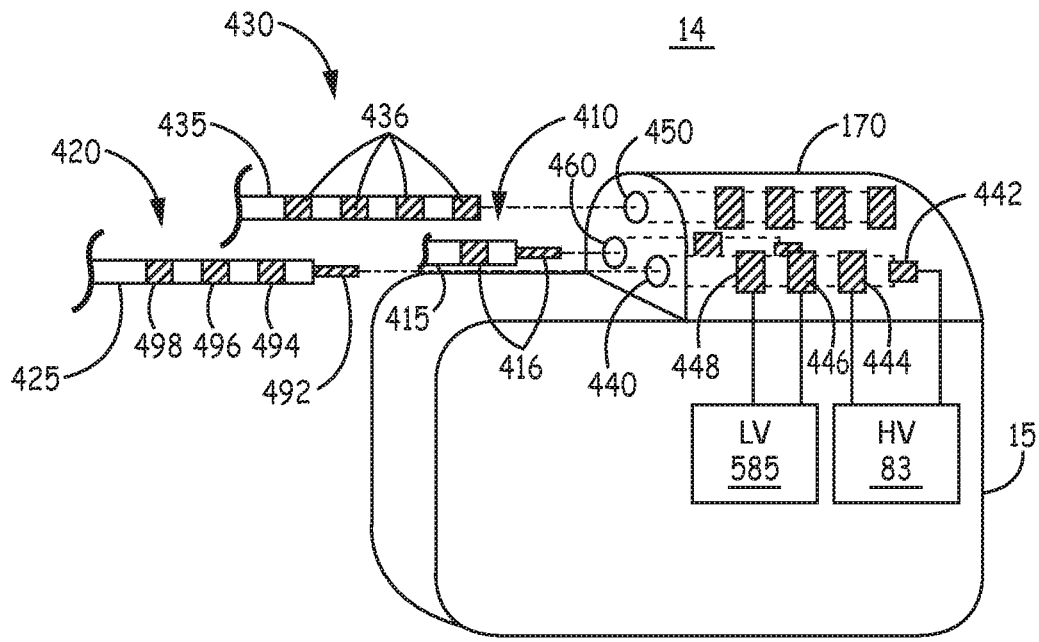
FIG. 12B is a conceptual diagram of the IMD and proximal portions of the transvenous leads shown in FIG. 11.

FIG. 12B is a conceptual diagram of IMD 14 and proximal portions of each of transvenous leads 410, 420 and 430 of FIG. 11, which carry the respective electrodes 412, 414, 422, 424, 426, 428, and 430 shown in FIG. 11. In this example, RV lead 420 includes an in-line quadripolar lead connector 425 configured to mate with connector bore 440, which may conform to the DF-4 industry standard. RV lead connector 425 is similar to extra-cardiovascular lead connector 470 described above, including a pin terminal 492 and three ring terminals 494, 496, and 498 configured to mate with corresponding contacts 442, 444, 446 and 448, respectively, of connector bore 440.

Pin terminal 492 and ring terminal 494 are electrically coupled to RV defibrillation electrode 426 and SVC defibrillation electrode 428 via elongated electrical connectors (not shown) extending through lead 420. Pin terminal 492 and ring terminal 494 are electrically coupled to HV therapy module 83 via contacts 442 and 444 when RV lead connector 425 is properly seated within connector bore 440 to enable HV therapy, e.g., CV/DF shocks, to be delivered via defibrillation electrodes 426 and/or 428. Ring terminals 496 and 498 are coupled to LV therapy module 585 when RV lead connector 425 is properly seated in connector bore 440, thereby electrically coupling RV pacing and sensing electrodes 422 and 424 (electrically coupled to terminals 496 and 498 via respective conductors extending through lead 420) to LV therapy module 585 via contacts 446 and 448.

RA lead 410 includes a proximal connector 415 having terminals 416, which may conform to the IS-1 industry standard, for mating with connector bore 460. Connector bore 460 includes a pair of contacts that make electrical contact with RA lead connector terminals 416 when RA lead connector 415 is properly seated in connector bore 460, thereby providing electrical connection between RA electrodes 412 and 414 (which are electrically coupled to terminals 416 via respective conductors extending through lead 410) and LV therapy module 585 for delivering RA pacing pulses.

CS lead 430 includes proximal connector 435, shown as an in-line, quadripolar connector having four connector terminals 436, which may conform to the IS-4 industry standard. When CS lead connector 435 is properly seated within connector bore 450, the electrodes 432 of CS lead 430 (FIG. 11) are electrically coupled to LV therapy module 585 via electrical connection between the CS lead connector terminals 436 and respective contacts of connector bore 450. It is understood that additional connections between the contacts of connector bores 440, 450 and 460 and other internal IMD circuitry such as electrical sensing module 86 and impedance measurement module 90 of FIG. 3 may be provided as needed but are not shown in FIG. 12B for the sake of clarity.

FIG. 13 is a conceptual diagram of LV therapy module 585 when IMD 14 is programmably configurable as a multi-channel pacing device for use with transvenous leads and electrodes (as shown in FIGS. 11 and 12b) or an extra-cardiovascular pacing device for use with an extra-cardiovascular lead and electrodes (as shown in the examples of FIGS. 1A-2C and FIG. 12A). Capacitor array 610 of LV therapy module 585 includes three pacing channels 602, 604 and 606 that may provide at least three separate pacing outputs when IMD 14 is programmed to operate as a multi-channel, multi-chamber pacemaker. For example, when IMD 14 is coupled to three transvenous leads 410, 420 and 430 as shown in FIG. 12B, the three pacing channels 602, 604 and 606 may be referred to as the left ventricular output channel 602 coupled to coronary sinus lead 430; the right ventricular output channel 604 coupled to RV lead 420, and the atrial output channel 606 coupled to RA lead 410. The three pacing channels 602, 604 and 606 are disconnected from one another by opening or disabling operation configuration switches 620a-620d (collectively 620) and 630 such that each channel 602, 604 and 606 delivers pacing pulses to a respective heart chamber along separate signal pacing output lines 642, 646 and 648, respectively, for delivering multi-chamber intra-cardiac pacing pulses.

IMD 14 may be programmed, however, to operate as a single channel extra-cardiovascular pacemaker. When programmed to operate as an extra-cardiovascular pacemaker the three pacing channels 602, 604 and 606 are tied together by closing operation configuration switches 620a-620d and 630 such that signal pacing output line 646 is used to deliver extra-cardiovascular pacing pulses, e.g., via extra-cardiovascular lead 16 as shown in the examples of FIGS. 1A-2B and FIG. 12A, when it is coupled to IMD 14 via connector bore 440.

Capacitor array 610 includes an array of four holding capacitors 612, 614, 616 and 618 which may be coupled to the three separate pacing channels 602, 604 and 606 when operation configuration switches 620 and 630 are open to enable multi-channel pacing. The control of capacitor array 610 by capacitor selection and control module 504 when IMD 14 is programmed to operate as a multi-channel pacemaker will be described first.

Beginning with pacing channel 602, a holding capacitor 612 and a back-up holding capacitor 614 are charged or topped off by LV charging circuit 514 during time intervals between left ventricular pacing pulses. Holding capacitor 612 may be selectively coupled to one of output capacitors 632a, 632b, 632c, and 632d via pace enable switch 622 and a selected one of respective cathode electrode selection switches 634a, 634b, 634c and 634d. Output lines 642a, 642b, 642c and 642d are coupled to respective ones of electrodes 436 carried by quadripolar coronary sinus lead 430 when lead 430 is connected to IMD 14 via connector bore 450 shown in FIG. 12B.

Electrode selection switches 634a-634d select which of the output capacitors 632a-632d of respective output signal lines 642a-642d is coupled to holding capacitor 612 for delivering a pacing pulse. Another one of electrodes 432 carried by coronary sinus lead 430 may be selected as a return anode electrode and coupled to ground. Capacitor selection and control module 504 controls switch 622 and one of electrode selection switches 634a through 634d to be closed for the duration of a left ventricular pacing pulse being delivered using coronary sinus lead 430. Back-up capacitor 614 is coupled to the selected output capacitor 632a, 632b, 632c or 632d via switch 624 when a back-up ventricular pacing pulse is needed, e.g., due to loss of capture detection.

Pacing channel 604 may be used for delivering right ventricular pacing pulses using RV lead 420. Holding capacitor 616 is coupled to output capacitor 636 along output line 646 when pace enable switch 626 is closed by capacitor selection and control module 504 according to RV pacing pulse timing information.

Pacing channel 606 may be used for delivering right atrial pacing pulses using RA lead 410. Holding capacitor 618 is discharged through output capacitor 638 on output line 648 when pace enable switch 628 is closed under the control of capacitor selection and control module 504 according to RA pacing pulse timing information received from pacing control module 102.

If IMD 14 is programmed to operate as an extra-cardiovascular pacemaker, capacitor selection and control module 504 closes operation configuration switches 620 and 630 so that all holding capacitors 612, 614, 616 and 618 can be discharged to output line 646 at appropriate times via respective output capacitors 632a-632d, 636 and 638. As shown in the example of FIG. 12A, when IMD 14 is used for delivering pacing pulses using extra-cardiovascular electrodes carried by lead 470, connector bores 450 and 460 may be sealed by plugs 480 and 482 such that all pacing current is directed to output line 646.

When programmed to deliver extra-cardiovascular pacing pulses, pacing channel 602 may be used to deliver one or more individual pulses of a composite pacing pulse by selectively closing electrode selection switches 634a-634d, one at a time or collectively at the same time, to discharge one of holding capacitors 612 or 614 or the combination of capacitors 612 and 614 across respective output capacitors 632a-632b to output line 646. If pacing channel 604 is selected to deliver an individual pulse, switch 626 is closed to discharge capacitor 616 across output capacitor 636. Likewise, if pacing channel 606 is selected to deliver an individual pulse of a composite pacing pulse, switch 628 is closed to discharge capacitor 618 across output capacitor 638 to output line 646.

In one example, holding capacitors 612, 614, 616 and 618 are 10 microfarad capacitors. Output capacitors 632a-632d, 636, and 638 are each 7 microfarad capacitors. One holding capacitor 612, 614, 616, or 618 in series with and one respective one output capacitor 632a, 632b, 632c, 632d, 636 or 638 has an effective capacitance of 4 microfarads. The maximum available pulse width for the effective capacitance of 4 microfarads may be set to 2 ms. Accordingly, an individual pulse may be delivered by discharging one holding capacitor 612 or 614 or 616 or 618 for up to 2 ms across one of output capacitors 632, 636 or 638, respectively.

If holding capacitor 612 and back-up holding capacitor 614 are selected in parallel by closing both of pace enable switches 622 and 624, and are discharged across all of the parallel output capacitors 632a-632d by closing all of selection switches 634a-634d, the effective capacitance is 12 microfarads in the example given above of each of holding capacitors 612 and 614 being 10 microfarads and output capacitors 632a-632d each being 7 microfarads. The maximum available individual pulse width may be set to 4 ms for this effective capacitance. The higher effective capacitance results in a longer RC time constant such that the maximum possible individual pulse width is longer than when the holding capacitors 612, 614, 616 or 618 are selected one at a time with one respective output capacitor selected from capacitors 632, 636 or 638.

Capacitor selection and control module 504 selects which holding capacitors 612, 614, 616 and 618 are coupled to output line 646 and in what combinations and sequence by controlling respective switches 622, 624, 626 and 628 and electrode selection switches 634a-634d of pacing channel 602. A sequence of pulses may be delivered to produce a composite pacing pulse by sequentially discharging holding capacitors 612, 614, 616 and 618 one at a time (or one combination at a time) across respective output capacitors 632a-d, 636 or 638 by sequentially enabling or closing the respective switches 622, 624, 626, 628. For example, at least two of holding capacitors 612, 614, 616 and 618 are sequentially discharged to produce a composite pacing pulse of at least two fused individual pulses.

Referring again to the example of FIG. 12A, output line 646 may be electrically coupled to a pacing cathode electrode carried by lead 470 via ring terminal 476, and a return anode electrode carried by lead 470 may be coupled to ground via ring terminal 478 during extra-cardiovascular pacing. The pacing cathode electrode and return anode electrode may correspond to electrodes 28A and 28B, respectively, as shown in FIG. 1A, for example, or any pacing electrode vector selected from among electrodes 24A, 24B, 28A, 28B, 30 and housing 15. In other examples, with reference to FIG. 2A (or 2B), one of electrodes 28A or 28B (or 28A' or 28B') may be selected as the pacing cathode and one of the defibrillation electrodes 24A or 24B (or 24A' or 24B') may be selected as the return anode.

In other examples, two pacing channels, e.g., channel 602 and 604, may be coupled together to output line 646 by enabling or closing switches 620 to enable sequential fused pulses to be delivered using holding capacitors 622, 624 and 626. Composite pacing pulses including at least two fused individual pulses may be delivered using the two channels 602 and 604 electrically coupled to output line 646. The third pacing channel 606 may be isolated from output line 646 by disabling or opening operation configuration switch 630. The third pacing channel, pacing channel 606 in this example, may remain separate and available for other pacing purposes. Alternatively, channels 604 and 606 may be coupled to output line 646 by enabling or closing operation configuration switch 630 and opening switches 620. In this case pacing channel 602 remains separate and available for other pacing purposes and channels 604 and 606 are tied together for delivering composite pacing pulses.

Figure 14:
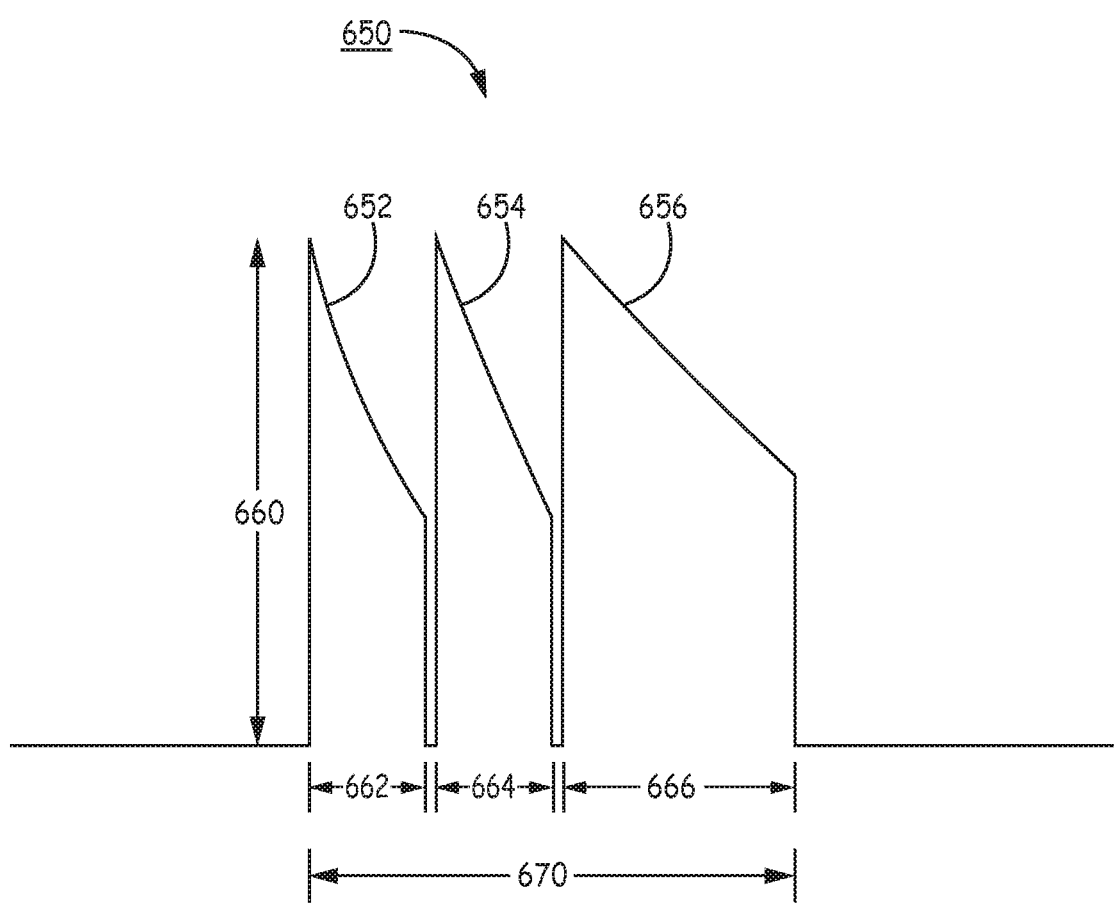
FIG. 14 is a conceptual diagram of an example of a composite pacing pulse that may be delivered by the low voltage therapy module of FIG. 13.

FIG. 14 is a conceptual diagram of one example of a composite pacing pulse 650 that may be delivered by LV therapy module 585 according to techniques disclosed herein. In this example, individual pulses 652, 654 and 656 have differing pulse widths. With reference to FIG. 13, pulse 652 may be delivered by discharging holding capacitor 616 across output capacitor 636 on output line 646 for an individual pulse width 662. Pulse 654 may be delivered by discharging holding capacitor 618 across output capacitor 638 to output line 646 for individual pulse width 664. In the illustrative example given above, when the effective capacitance of one holding capacitor 616 or 618 and the respective output capacitor 636 or 638 is 4 microfarads, the pulses 652 and 654 may each be 2 ms in pulse width.

The last individual pulse 656 has a pulse width 666 that is longer than pulse widths 662 and 664 and may be delivered using a larger effective capacitance than the capacitance used to deliver pulses 652 and 654. Continuing the illustrative example given above, if parallel 10 microfarad holding capacitors 612 and 614 are used to deliver pulse 656 across all of the 7 microfarad output capacitors 632a-632d in parallel, the effective capacitance is 12 microfarads. The pulse width 666 may be set to 4 ms, longer than pulse widths 662 and 664. The composite pacing pulse width 670 is 8 ms in this example.

The leading pulse amplitude 660 of each pulse 652, 654 and 656 may be programmable to any of a range of pulse amplitudes, e.g., 1 V, 2 V, 4 V, 6 V, and 8 V. The pulse amplitude 660 may be selected to be greater than the pacing amplitude capture threshold when the composite pulse width 670 is 8 ms. A non-zero gap between each pulse 652, 654 and 656 may occur due to limitations of the electronics, but pulses 652, 654 and 656 are delivered close enough in time to provide a cumulative delivered pulse energy within the composite pacing pulse width 670 that is greater than the pacing capture threshold even when each pulse 652, 654 and 656 individually have a pulse energy that is less than the pacing capture threshold of the patient's heart.

In other examples, longer pulse 656 may be delivered first with one or more shorter pulses 652 and 654 following, or longer pulse 656 may be delivered between shorter pulses 652 and 654. It is recognized that numerous combinations of individual pulse number, individual pulse widths and individual pulse sequences can be conceived for delivering a composite pacing pulse utilizing varying effective capacitances for each individual pulse selected from a capacitor array including multiple holding and output capacitors, which may have differing capacitance values, without departing from the scope of the extra-cardiovascular pacing techniques disclosed herein. Negative-going recharge pulses are not shown in FIG. 14 but it is to be understood that composite pacing pulse 650 may be a biphasic composite pacing pulse having a negative-going portion similar to that of composite pacing pulse 50 of FIG. 4A having recharge pulses 70.

Figure 15:
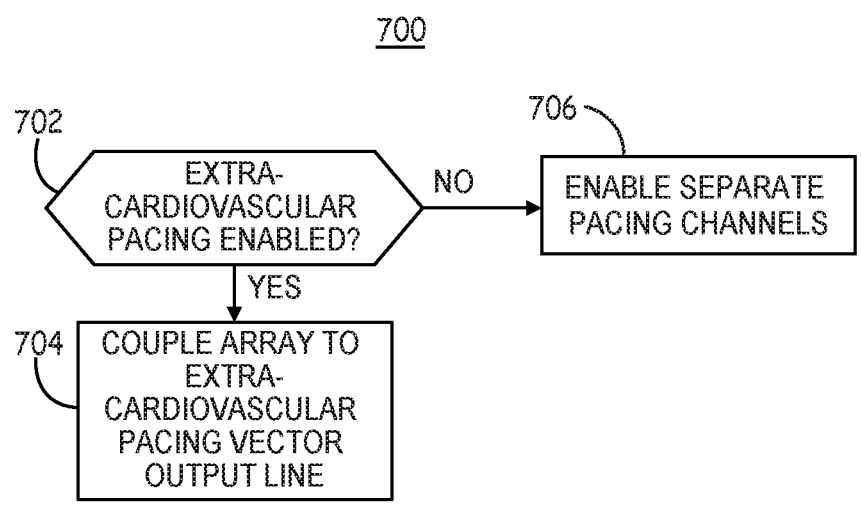
FIG. 15 is a flow chart of a method for programmably configuring the IMD of FIG. 11 to operate to deliver either multi-channel, multi-chamber cardiac pacing in conjunction with transvenous leads or to deliver single-channel cardiac pacing in conjunction with an extra-cardiovascular lead and extra-cardiovascular electrodes.

FIG. 15 is a flow chart 700 of a method for programmably configuring IMD 14 to operate as either a multi-channel, multi-chamber pacemaker in conjunction with transvenous leads or as a single-channel pacemaker in conjunction with an extra-cardiovascular lead and extra-cardiovascular electrodes. If control module 80 receives a user command via telemetry module 88 (FIG. 3) indicating that extra-cardiovascular pacing should be enabled, as determined at block 702, the capacitor array 610 (FIG. 13) is configured to enable sequential pacing pulses on a single output line 646. At block 704, control module 80 sends control signals to capacitor selection and control module 504 (FIG. 13) to enable or close operation configuration switches 620 and 630 so that all holding capacitors 612, 614, 616 and 618 can be selectively coupled to output line 646 at appropriate times for discharging across an extra-cardiovascular pacing electrode vector coupled to output line 646. Output lines 642a-642d and 648 are tied to output line 646 by holding operation configuration switches 620a-620d and 630 in closed or enabled states at block 704.

If extra-cardiovascular pacing is not enabled by a user command at block 702, control module 80 controls capacitor selection and control module 504 to hold switches 620a-620d and 630 in an open or disabled state so that holding capacitors 612, 614 and 618 cannot be coupled to output line 646 during pacing. Electrode selection switches 634a-634d are selectively opened or closed to enable pacing channel 602 to deliver pacing pulses to electrode(s) coupled to respective output lines 642a-642d. When operation configuration switches 620a-620d and 630 are held in an open state, pacing channel 606 is enabled for pacing pulse delivery on output line 648 using holding capacitor 618 and output capacitor 638. Pacing channel 604 is enabled for pacing pulse delivery on output line 646 using holding capacitor 616 and output capacitor 636.

In some examples, control module 80 automatically determines whether extra-cardiovascular pacing should be enabled at block 702 based upon automatic detection of electrodes coupled to connector bores 440, 450 and 460 rather than based on a user-entered command. Automatic detection of electrodes coupled to connector bores 440, 450 and 460 may be based on impedance measurements by impedance measurement module 90. When impedance measurements are high indicating an open circuit condition across connectors included in connector bores 450 and 460, an extra-cardiovascular pacing configuration is enabled at block 704. When impedance measurements are relatively lower indicating connection of a lead and electrodes within connector bores 450 and 460, multi-channel pacing configuration is enabled at block 706.

The operation configuration switches 620a-620d and 630 may be set a single time to a closed or enabled state for single channel extra-cardiovascular pacing or to an open or disabled state for multi-channel pacing and remain in that state for the duration of the operational life of IMD 14. The operation configuration of IMD 14 may be set at the time of manufacture or set by a user based on the intended use of IMD 14. It may be assumed that IMD 14 will be used only as multi-channel pacemaker with transvenous leads or only as a single-channel extra-cardiovascular pacemaker for the duration of its useful life. In other examples, if a patient's therapeutic needs change, the lead(s) and electrodes coupled to IMD 14 may be removed and replaced with a different lead(s) and electrodes and the operational configuration of IMD 14 may be programmably (manually or automatically) changed as needed. For example, single channel extra-cardiovascular pacing may be adequate for a patient initially and at a later time multi-channel pacing may be required for providing multi-chamber pacing therapy due to a change in the patient's disease state. A single extra-cardiovascular lead 470 as shown in FIG. 12A may be replaced with the transvenous three lead system as shown in FIG. 12B, and IMD 14 may be programmed to change its operational configuration from the single-channel extra-cardiovascular configuration to the multi-channel configuration for use with the transvenous leads 410, 420 and 430.

Thus, a method and apparatus for delivering pacing pulses using extra-cardiovascular electrodes have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An implantable medical device, comprising:
 a therapy module having a capacitor array comprising a plurality of capacitors and an output signal line, the therapy module configured to selectively couple the capacitor array to the output signal line to generate a composite pacing pulse;
 an impedance measurement module; and
 a pacing control module coupled to the therapy module and the impedance measurement module and configured to control the therapy module to sequentially discharge at least a portion of the plurality of capacitors to produce a series of at least two individual pulses that define the composite pacing pulse,
 the pacing control module further configured to:
  select a capacitance element from the plurality of capacitors of the capacitor array;
  obtain an impedance measurement by the impedance measurement module;
  determine an RC time constant from the impedance measurement and an effective capacitance of the selected capacitance element;
  set an individual pulse width based on at least the determined RC time constant; and
  control the therapy module to produce one of the at least two individual pulses using the selected capacitance element and having the individual pulse width.

2. The device of claim 1, wherein the pacing control module is configured to control the therapy module to:
 start discharging a first portion of the plurality of capacitors to produce a leading edge of a first one of the individual pulses and stop discharging the first portion of the plurality of capacitors to produce a terminating edge of the first one of the individual pulses; and
 start discharging a second portion of the plurality of capacitors different than the first portion to produce a second one of the individual pulses upon the terminating edge of the first one of the individual pulses.

3. The device of claim 1, wherein the pacing control module is configured to control the therapy module to deliver each of the at least two individual pulses with a respective individual pulse energy that is less than a pacing capture threshold.

4. The device of claim 1, wherein the pacing control module is configured to control the therapy module to deliver the at least two individual pulses that define the composite pacing pulse with a cumulative pulse energy that is greater than a pacing capture threshold.

5. The device of claim 1, wherein the pacing control module is configured to:
select a pacing pulse width for the composite pacing pulse;
select a sequence of capacitance elements from the plurality of capacitors of the capacitor array;
set an individual pulse width for each capacitance element of the sequence so that a sum of the individual pulse widths is equal to or greater than the selected pacing pulse width; and
control the therapy module to:
charge each of the capacitance elements of the sequence to a pulse voltage amplitude; and
produce the series of the at least two individual pulses by sequentially discharging each of the capacitance elements of the sequence for the respective individual pulse width set for the respective capacitance element.

6. The device of claim 1, wherein:
the plurality of capacitors of the capacitor array comprise at least two holding capacitors; and
the pacing control module is configured to control the therapy module to sequentially discharge the at least two holding capacitors one at a time to produce the series of at least two individual pulses.

7. The device of claim 1, wherein:
the plurality of capacitors of the capacitor array comprises at least four holding capacitors; and
the pacing control module is configured to control the therapy module to sequentially discharge the at least four holding capacitors to produce a series of at least three individual pulses.

8. The device of claim 1, wherein the pacing control module is configured to control the therapy module to deliver a first one of the at least two individual pulses having a first pulse width and a second one of the at least two individual pulses having a second pulse width that is greater than the first pulse width.

9. The device of claim 1, further comprising:
a plurality of operation configuration switches and a plurality of pacing output lines;
wherein the plurality of capacitors comprises a plurality of holding capacitors and a plurality of output capacitors, each of the plurality of output capacitors along a respective one of the plurality of pacing output lines;
wherein the control module is configured to enable extra-cardiovascular pacing using composite pacing pulses by the therapy module by controlling the plurality of operation configuration switches to couple at least a portion of the plurality of output capacitors to a single one of the plurality of pacing output lines.

10. The device of claim 9, wherein:
the control module is configured to disable extra-cardiovascular pacing using composite pacing pulses and enable multi-channel pacing by the therapy module by controlling the plurality of operation configuration switches to uncouple at least a portion of the plurality of output capacitors from the single one of the plurality of pacing output lines.

11. The device of claim 1, further comprising:
a housing enclosing the therapy delivery module and the pacing control module;
a connector block coupled to the housing and comprising at least one connector bore configured to receive a proximal connector of an extra-cardiovascular lead for electrically coupling at least one electrode of the extra-cardiovascular lead to the output signal line.

12. The device of claim 1, wherein the pacing control module is further configured to control the therapy module to sequentially discharge a first portion of the plurality of capacitors for a first individual pulse width and discharge a second portion of the plurality of capacitors for a second individual pulse width, the first and second individual pulse widths defining a composite pacing pulse width of at least four milliseconds.

13. The device of claim 1, wherein the pacing control module is further configured to control the therapy module to:
charge a first portion of the plurality of capacitors to a voltage amplitude;
charge a second portion of the plurality of capacitors to the voltage amplitude; and
discharge the first portion of the plurality of capacitors to deliver a first individual pulse of the at least two individual pulses having the voltage amplitude; and
discharge the second portion of the plurality of capacitors to deliver a second individual pulse of the at least two individual pulses after the first individual pulse and having the voltage amplitude.

14. An implantable medical device, comprising:
a therapy module having a capacitor array comprising a plurality of capacitors and an output signal line, the therapy module configured to selectively couple the capacitor array to the output signal line to generate a composite pacing pulse;
a pacing control module coupled to the therapy module and configured to control the therapy module to sequentially discharge at least a portion of the plurality of capacitors to produce a series of at least two individual pulses that define the composite pacing pulse; and
an impedance measurement module,
the pacing control module further configured to:
select a capacitance element from the plurality of capacitors of the capacitor array;
obtain an impedance measurement by the impedance measurement module;
determine an RC time constant from the impedance measurement and an effective capacitance of the selected capacitance element;
determine an individual pulse width based at least on the determined RC time constant; and
determine a number of individual pulses to be produced in the series based on the individual pulse width so that the individual pulses have a cumulative pulse width that is greater than a pacing pulse width capture threshold.

15. An implantable medical device, comprising:
a therapy module having a capacitor array comprising a plurality of capacitors and an output signal line, the therapy module configured to selectively couple the capacitor array to the output signal line to generate a composite pacing pulse;
a pacing control module coupled to the therapy module and configured to control the therapy module to sequentially discharge at least a portion of the plurality of capacitors to produce a series of at least two individual pulses that define the composite pacing pulse; and an analog-to-digital converter configured to sample an amplitude of the composite pacing pulse, the pacing control module further configured to:
compare the sampled amplitude of the composite pacing pulse to an amplitude threshold, and
control the therapy module to start a next one of the series of at least two individual pulses in response to the sampled amplitude falling to or below the amplitude threshold.

16. An implantable medical device, comprising:
a therapy module having a capacitor array comprising a plurality of capacitors and an output signal line, the therapy module configured to selectively couple the capacitor array to the output signal line to generate a composite pacing pulse;
a pacing control module coupled to the therapy module and configured to control the therapy module to sequentially discharge at least a portion of the plurality of capacitors to produce a series of at least two individual pulses that define the composite pacing pulse; and
an analog-to-digital converter configured to sample an amplitude of the composite pacing pulse;
the control module further configured to:
compare the sampled amplitude to an amplitude threshold;
select a capacitance element for producing a next one of the at least two individual pulses based on the comparison by selecting a first capacitance element having a first effective capacitance in response to the sampled amplitude being greater than the amplitude threshold and selecting a second capacitance element having a second effective capacitance greater than the first effective capacitance in response to the sampled amplitude being less than the amplitude threshold.

17. An implantable medical device, comprising:
a therapy module having a capacitor array comprising a plurality of capacitors and a output signal line, the therapy module configured to selectively couple the capacitor array to the output signal line to generate a composite pacing pulse; and
a pacing control module coupled to the therapy module and configured to control the therapy module to sequentially discharge at least a portion of the plurality of capacitors to produce a series of at least two individual pulses that define the composite pacing pulse,
wherein the pacing control module is further configured to:
set a pacing timing interval by setting one of a bradycardia pacing interval, an asystole pacing interval, a post-shock pacing interval, an anti-tachycardia pacing interval, an entrainment pacing interval prior to a tachyarrhythmia induction shock, or a tachyarrhythmia induction burst interval; and
control the therapy module to deliver the composite pacing pulse at the expiration of the pacing timing interval.

18. A method performed by an implantable medical device, comprising:
controlling a therapy module to selectively couple a capacitor array comprising a plurality of capacitors to an output signal line; and controlling the therapy module by a pacing control module to generate a composite pacing pulse by sequentially discharging at least a portion of the plurality of capacitors to produce a series of at least two individual pulses that define the composite pacing pulse,
wherein controlling the therapy module to generate the composite pacing pulse further comprises:
selecting a capacitance element from the plurality of capacitors of the capacitor array;
obtaining an impedance measurement by an impedance measurement module of the implantable medical device;
determining an RC time constant from the impedance measurement and an effective capacitance of the selected capacitance element;
setting an individual pulse width based on at least the determined RC time constant; and
controlling the therapy module to produce one of the at least two individual pulses using the selected capacitance element and having the individual pulse width.

19. The method of claim 18, further comprising:
starting discharging of a first portion of the plurality of capacitors to produce a leading edge of a first one of the individual pulses and stopping discharging of the first portion of the plurality of capacitors to produce a terminating edge of the first one of the individual pulses; and
starting discharging of a second portion of the plurality of capacitors different than the first portion to produce a second one of the individual pulses upon the terminating edge of the first one of the individual pulses.

20. The method of claim 18, further comprising controlling the therapy module to deliver each of the at least two individual pulses with a respective individual pulse energy that is less than a pacing capture threshold.

21. The method of claim 18, wherein the pacing control module is configured to control the therapy module to deliver the at least two individual pulses that define the composite pacing pulse with a cumulative pulse energy that is greater than a pacing capture threshold.

22. The method of claim 18, further comprising:
selecting a pacing pulse width for the composite pacing pulse;
selecting a sequence of capacitance elements from the plurality of capacitors of the capacitor array;
setting an individual pulse width for each capacitance element of the sequence so that a sum of the individual pulse widths is equal to or greater than the selected pacing pulse width;
charging each of the capacitance elements of the sequence to a pulse voltage amplitude; and
producing the series of the at least two individual pulses by sequentially discharging each of the capacitance elements of the sequence for the respective individual pulse width set for the respective capacitance element.

23. The method of claim 18, wherein sequentially discharging at least the portion of the plurality of capacitors comprises sequentially discharging at least two holding capacitors one at a time to produce the series of at least two individual pulses.

24. The method of claim 18, wherein sequentially discharging at least the portion of the plurality of capacitors comprises sequentially discharging at least four holding capacitors to produce a series of at least three individual pulses.

25. The method of claim 18, further comprising delivering a first one of the at least two individual pulses having a first pulse width and a second one of the at least two individual pulses having a second pulse width that is greater than the first pulse width.

26. The method of claim 18, further comprising:
enabling extra-cardiovascular pacing by the therapy module using composite pacing pulses by controlling a plurality of operation configuration switches of the therapy module to couple at least a portion of a plurality of output capacitors of the therapy module to a single one of a plurality of pacing output lines.

27. The method of claim 26, further comprising disabling extra-cardiovascular pacing using composite pacing pulses and enabling multi-channel pacing by the therapy module by controlling the plurality of operation configuration switches to uncouple at least a portion of the plurality of output capacitors from the single one of the plurality of pacing output lines.

28. The method of claim 18, further comprising delivering the composite pacing pulse by an extra-cardiovascular electrode carried by an extra-cardiovascular lead coupled to the therapy delivery module via a connector block coupled to a housing of the implantable medical device and enclosing the therapy.

29. A method performed by an implantable medical device, comprising:
controlling a therapy module to selectively couple a capacitor array comprising a plurality of capacitors to an output signal line; and
controlling the therapy module by a pacing control module to generate a composite pacing pulse by sequentially discharging at least a portion of the plurality of capacitors to produce a series of at least two individual pulses that define the composite pacing pulse,
wherein controlling the therapy module to generate the composite pacing pulse further comprises:
selecting a capacitance element from the plurality of capacitors of the capacitor array;
obtaining an impedance measurement by the impedance measurement module;
determining an RC time constant from the impedance measurement and an effective capacitance of the selected capacitance element;
determining an individual pulse width based at least on the determined RC time constant; and
determining a number of individual pulses to be produced in the series based on the individual pulse width so that the individual pulses have a cumulative pulse width that is greater than a pacing pulse width capture threshold.

30. A method performed by an implantable medical device, comprising:
controlling a therapy module to selectively couple a capacitor array comprising a plurality of capacitors to an output signal line; and
controlling the therapy module by a pacing control module to generate a composite pacing pulse by sequentially discharging at least a portion of the plurality of capacitors to produce a series of at least two individual pulses that define the composite pacing pulse,
wherein controlling the therapy module to generate the composite pacing pulse further comprises:
sampling an amplitude of the composite pacing pulse;
comparing the sampled amplitude of the composite pacing pulse to an amplitude threshold, and
controlling the therapy module to start a next one of the series of at least two individual pulses in response to the sampled amplitude falling to or below the amplitude threshold.

31. A method performed by an implantable medical device, comprising:
controlling a therapy module to selectively couple a capacitor array comprising a plurality of capacitors to an output signal line; and
controlling the therapy module by a pacing control module to generate a composite pacing pulse by sequentially discharging at least a portion of the plurality of capacitors to produce a series of at least two individual pulses that define the composite pacing pulse,
wherein controlling the therapy module to generate the composite pacing pulse further comprises:
sampling an amplitude of the composite pacing pulse;
comparing the sampled amplitude to an amplitude threshold; and
selecting a capacitance element for delivering a next one of the at least two individual pulses based on the comparison by selecting a first capacitance element having a first effective capacitance in response to the sampled amplitude being greater than the amplitude threshold and selecting a second capacitance element having a second effective capacitance greater than the first effective capacitance in response to the sampled amplitude being less than the amplitude threshold.

32. A method performed by an implantable medical device, comprising:
controlling a therapy module to selectively couple a capacitor array comprising a plurality of capacitors to an output signal line;
controlling the therapy module by a pacing control module to generate a composite pacing pulse by sequentially discharging at least a portion of the plurality of capacitors to produce a series of at least two individual pulses that define the composite pacing pulse;
setting a pacing timing interval by setting one of a bradycardia pacing interval, an asystole pacing interval, a post-shock pacing interval, an anti-tachycardia pacing interval, an entrainment pacing interval prior to a tachyarrhythmia induction shock, or a tachyarrhythmia induction burst interval; and
controlling the therapy module to deliver the composite pacing pulse at the expiration of the pacing timing interval.

* * * * *